United States Patent
Persen et al.

(10) Patent No.: US 12,290,368 B2
(45) Date of Patent: *May 6, 2025

(54) DETECTION OF ATRIAL FIBRILLATION

(71) Applicant: HEARTBEAM, INC., Santa Clara, CA (US)

(72) Inventors: Ken Persen, Irvine, CA (US); Ross Grady Baker, Jr., Irvine, CA (US); Lucy Zhuang, Irvine, CA (US); Jon Kaneshiro, Irvine, CA (US)

(73) Assignee: HEARTBEAM, INC., Santa Clara, CA (US)

( * ) Notice: Subject to any disclaimer, the term of this patent is extended or adjusted under 35 U.S.C. 154(b) by 137 days.

This patent is subject to a terminal disclaimer.

(21) Appl. No.: 17/887,160

(22) Filed: Aug. 12, 2022

(65) Prior Publication Data

US 2022/0386929 A1 Dec. 8, 2022

Related U.S. Application Data

(63) Continuation of application No. 16/368,568, filed on Mar. 28, 2019, now Pat. No. 11,412,972.

(60) Provisional application No. 62/649,530, filed on Mar. 28, 2018.

(51) Int. Cl.
| | |
|---|---|
| *A61B 5/361* | (2021.01) |
| *A61B 5/024* | (2006.01) |
| *A61B 5/0245* | (2006.01) |

(52) U.S. Cl.
CPC .......... *A61B 5/361* (2021.01); *A61B 5/02438* (2013.01); *A61B 5/02455* (2013.01)

(58) Field of Classification Search
CPC . A61B 5/361; A61B 5/02438; A61B 5/02455; A61B 5/721; A61B 5/681; A61B 5/7264; A61B 5/7282; A61B 5/0245; A61B 5/7225; A61B 5/02416; G16H 50/20
See application file for complete search history.

(56) References Cited

U.S. PATENT DOCUMENTS

| | | | |
|---|---|---|---|
| 11,412,972 B2* | 8/2022 | Persen | A61B 5/02416 |
| 2014/0221845 A1* | 8/2014 | Mestha | A61B 5/02416 |
| | | | 600/479 |

OTHER PUBLICATIONS

Kikillus et al "Three different algorithms for identifying patients suffering from atrial fibrillation during atrial fibrillation free phases of the ECG" 2007.*

* cited by examiner

*Primary Examiner* — Mark W. Bockelman
(74) *Attorney, Agent, or Firm* — PatentVest, Inc.; Matthew L. Bycer

(57) ABSTRACT

Systems, methods, and computer software for detecting atrial fibrillation are described. Photoplethysmographic (PPG) signal data may be received as communicated by a PPG sensor of a wearable device worn by a user. Heartbeats from a portion of the PPG signal data may be determined and a heart rhythm type may be determined based on at least the heartbeats. A determination of whether the heart rhythm type includes Atrial Fibrillation (AF) may be made, and, when AF is detected, an AF detection alert may be displayed at the wearable device.

15 Claims, 14 Drawing Sheets

DETECTION OF ATRIAL FIBRILLATION

RELATED APPLICATION(S)

This application is a continuation of and claims priority to and the benefit of U.S. application Ser. No. 16/368,568 filed Mar. 28, 2019, titled "Detection of Atrial Fibrillation," which claims priority to U.S. Provisional Application No. 62/649,530, filed Mar. 28, 2018, titled "Systems and Methods for Detection of Atrial Fibrillation," the disclosures of each are hereby incorporated by reference.

DESCRIPTION OF THE RELATED ART

Electrical and physiological characteristics of the human heart can be measured using, for example, sensors such as electrocardiogram (ECG) sensors or photoplethysmograph (PPG) sensors. Signals from such sensors may then be analyzed to determine useful and informative health states of a patient, such as heart rates, particular heart rhythms, and the like.

SUMMARY

Systems, methods, and computer program products are disclosed that may be used to detect atrial fibrillation. For example, photoplethysmographic (PPG) signal data may be received as communicated by a PPG sensor of a wearable device worn by a user. Heartbeats from a portion of the PPG signal data may be determined and a heart rhythm type may be determined based on at least the heartbeats. A determination of whether the heart rhythm type includes Atrial Fibrillation (AF) may be made, and, when AF is detected, an AF detection alert may be displayed at the wearable device.

In some variations, an occupancy metric can be determined based partially on an interval scatter analysis, where determining the heart rhythm type can further include utilization of the occupancy metric. The occupancy metric can be determined by determining points that represent heartbeat interval changes over a period of time, defining bins into which the points may fall, and determining a fraction of bins that contain at least one of the points. The points can represent a change between two adjacent heartbeat intervals and the period of time can also be based on a moving window.

In other variations, a distance metric can be determined based at least partially on points representing heartbeat interval changes, where determining the heart rhythm type can further include utilization of the distance metric. The distance metric can be determined by operations including determining points that represent heartbeat interval changes over a period of time and determining the distance metric by determining a median of distances between the points. The distances can be determined between consecutive points and the period of time can be based on a moving window.

In yet other variations, an interval variability metric can be determined based on heartbeat intervals derived from the heartbeats, where determining the heart rhythm type can further include utilization of the interval variability metric. The interval variability metric can be a median of absolute changes in heartbeat intervals and the heartbeat intervals can be included within a moving window.

In some variations, determining whether the heart rhythm type includes Atrial Fibrillation can include utilization of an occupancy metric, a distance metric, and an interval variability metric.

In other variations, displaying of the AF detection alert can occur when AF has been determined based on a number of heartbeats greater than an AF detection alert threshold. The operations can also further include receiving a patient identification communicated by the wearable device and generating the AF detection alert when an authorization is received that indicates a permission to display AF detection alerts to the user.

Implementations of the current subject matter can include, but are not limited to, methods consistent with the descriptions provided herein as well as articles that comprise a tangibly embodied machine-readable medium operable to cause one or more machines (e.g., computers, etc.) to result in operations implementing one or more of the described features. Similarly, computer systems are also contemplated that may include one or more processors and one or more memories coupled to the one or more processors. A memory, which can include a computer-readable storage medium, may include, encode, store, or the like, one or more programs that cause one or more processors to perform one or more of the operations described herein. Computer implemented methods consistent with one or more implementations of the current subject matter can be implemented by one or more data processors residing in a single computing system or across multiple computing systems. Such multiple computing systems can be connected and can exchange data and/or commands or other instructions or the like via one or more connections, including but not limited to a connection over a network (e.g., the internet, a wireless wide area network, a local area network, a wide area network, a wired network, or the like), via a direct connection between one or more of the multiple computing systems, etc.

The details of one or more variations of the subject matter described herein are set forth in the accompanying drawings and the description below. Other features and advantages of the subject matter described herein will be apparent from the description and drawings, and from the claims. While certain features of the currently disclosed subject matter are described for illustrative purposes in relation to particular implementations, it should be readily understood that such features are not intended to be limiting. The claims that follow this disclosure are intended to define the scope of the protected subject matter.

BRIEF DESCRIPTION OF THE DRAWINGS

The accompanying drawings, which are incorporated in and constitute a part of this specification, show certain aspects of the subject matter disclosed herein and, together with the description, help explain some of the principles associated with the disclosed implementations.

DETAILED DESCRIPTION

The subject matter described herein relates systems, methods and software for monitoring the heath of a user and providing the user with health guidance.

Figure 1:
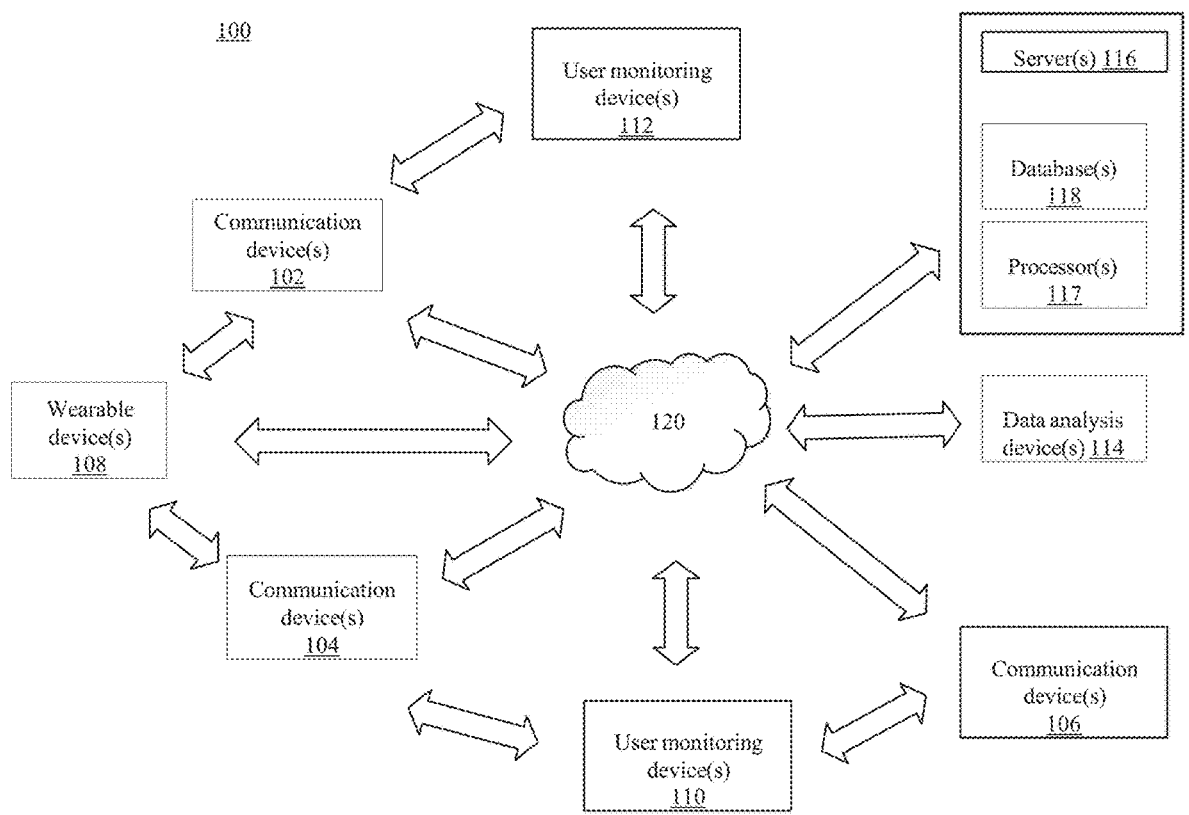
FIG. 1 illustrates an exemplary system that can provide for the monitoring of user health characteristics and provide health-related guidance in accordance with certain aspects of the present disclosure.

FIG. 1 illustrates an exemplary system 100 that can provide for the monitoring of health characteristics of a user (for example, a human patient, or other living organism) and can provide health guidance to the user based on the health characteristics monitoring.

In some implementations, the exemplary system 100 depicted in FIG. 1 may include elements such as user wearable device(s) 108 (e.g., a smart watch), communication devices 102, 104, and 106 (e.g., a mobile phone or PC), user monitoring devices 110 and 112 (e.g., a separate smart scale or blood glucose monitor), data analysis device(s) 114, server(s) 116 (e.g., including processor(s) 117 and database(s) 118), and network(s) 120. The server(s) 116 and devices illustrated in FIG. 1 may include communication lines or ports to enable the exchange of information within a network (e.g., network 120), or within other computing platforms via wired or wireless techniques (e.g., Ethernet, fiber optics, coaxial cable, WiFi, Bluetooth, near field communication, or other technologies).

It should be noted that, while one or more operations are described herein as being performed by particular components of system 100, those operations may, in some embodiments, be performed by other components of system 100. As an example, while one or more operations are described herein as being performed by components of data analysis device(s) 114, those operations may, in other embodiments, be performed by components of the user wearable device(s) 108, by components of the communications devices 102, 104, and 106, and/or by other components of system 100.

The user wearable device(s) 108 may be a smart watch (for example, Samsung's Gear, the Apple Watch, etc.), or any other device that a user can wear. A user wearable device 108 may include one or more sensors that are integrated within the device. For example, a user wearable device 108 that is a smart watch may include motion sensors (for example, accelerometers), bio-impedance sensors, ECG sensors, ballistocardiogram sensors, acoustic sensors (for example, ultrasound), photo plethysmograph (PPG) sensors that use light-based technology to sense a rate of blood flow, and other sensors. Wearable device 108 may also be considered herein to include sensors that are worn on a user's body but not integrated within the main wearable portion (for example, an ECG sensor worn on a user's chest that is not integrated with a smart watch, but which nevertheless communicates with the smart watch).

Figure 2:
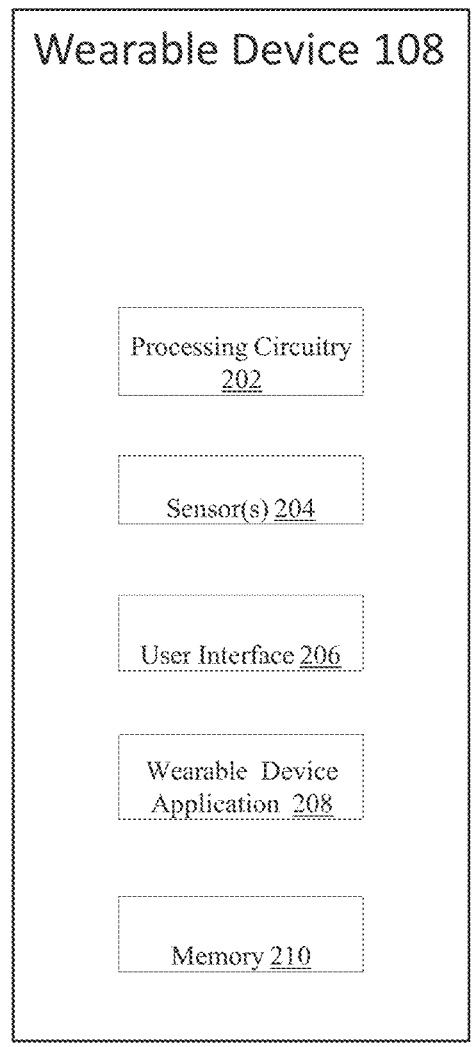
FIG. 2 illustrates an implementation of a user wearable device in accordance with certain aspects of the present disclosure.

FIG. 2 illustrates wearable device 108, including processing circuitry 202, sensor(s) 204, wearable user interface 206, wearable device application 208, and memory 210. As noted, sensor(s) 204 may include multiple sensors integrated with the main wearable portion of the device and/or sensors located elsewhere on the user's body. The wearable device application 208, and signals from sensor(s) 204, may be stored in memory 210.

A user may interact with wearable user interface 206, for example, to enter data such as age, height, weight and gender, or to view measured or calculated metrics such as heart rate, pulse rate variability, stress level, breathing guidance, and the like.

Wearable device application 208 may run on processing circuitry 202 and perform such operations as receiving signals from sensor(s) 204, calculating various health characteristics, outputting the display of information, providing health guidance to the user, etc.

Wearable device 108 may undergo certain configurations during a calibration period. For example, a user may wear device 108 for a 24-hour calibration period upon first use to allow for the collection of user information from sensor(s) 204. For example, the collection of characteristics such as pulse rate or respiration rate over a period of time may facilitate device calibration and provide user information helpful in the future analysis of signals and the provision of health guidance to the user. In some beneficial implementations, the calibration may be performed while the user is wearing a single lead ECG or other sensor(s) for reference purposes.

Communication devices 102, 104, and 106 may include any type of mobile or fixed device, for example, a desktop computer, a notebook computer, a smartphone, a tablet, or other communication device. Users may, for instance, utilize one or more communication devices 102, 104, and 106 to interact with one another, with one or more wearable devices, one or more servers, or other components of system 100.

Figure 3:
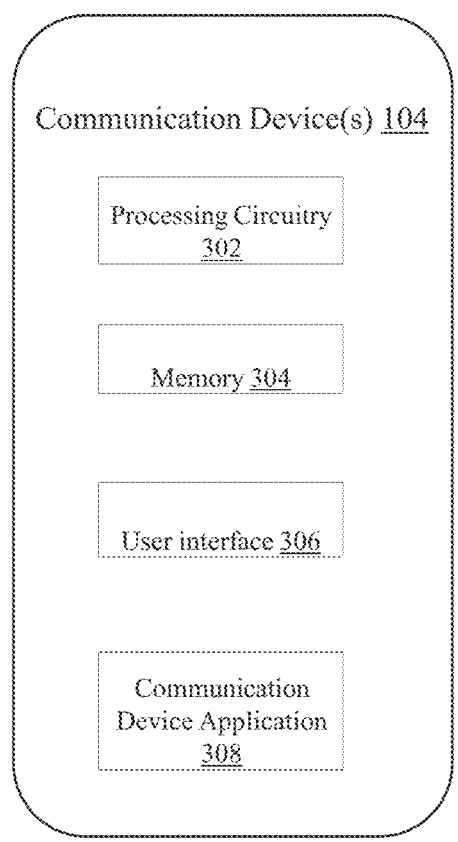
FIG. 3 illustrates an implementation of a communication device in accordance with certain aspects of the present disclosure.

FIG. 3 illustrates some components of an exemplary communication device 104, including processing circuitry 302, memory 304, user interface 306, and communication device application 308. The processing circuitry 302, memory 304, and user interface 306 function similarly to the processing circuitry 202, memory 210, and user interface 206, respectively, in FIG. 2, although the application and user interface of a communication device will commonly have greater functionality than that of a wearable device.

In some implementations, communication device application 308 may be a mobile application (for example, a smartphone application), or a web application. The communication device application 308, in some implementations, can communicate with the user wearable device application 208 via Bluetooth (or any other method of wired or wireless communication) and/or may transmit measurements for archival and post-processing to a cloud-based database (for example, database(s) 118). The communication device application 308 may aggregate data from the other sensors (for example, from user monitoring devices 110 and 112), perform pre-transmission processing locally, and transmit data for further processing or viewing.

In some implementations, user monitoring devices 110 and 112 may include a blood pressure monitoring device (for example, a blood pressure cuff), a weight monitoring device (for example, a scale), a blood glucose monitoring device, etc. User monitoring devices 110 and 112 may measure health states of the user different from the health states measured by user wearable device(s) 108.

The health monitoring and guidance systems and methods detailed herein typically utilize signals coming from one or more sensors that may be in contact with a user's body and that are sensing information relevant to the user. Sensors can be integrated with a wearable device, communicating with a wearable device, or can instead be separate from a wearable device and communicating with system 100 through other components.

As discussed further herein, system 100 can include components and methods for acquiring particular signals, for processing such signals (e.g., noise reduction), and for modifying signal acquisition methods. Each of these activities may be performed by any of the components of system 100.

In one implementation, a user wearable device 108 may capture an optical signal (for example, a pulse signal) from optical sensor(s) utilizing green and/or an infrared wavelengths. Wearable device 108 may also capture a motion signal that could be used to assess noise or interference resulting from motion of a user wearing device 108 or to assess other parameters relevant to health analysis and guidance.

In some implementations, the optical signal and the motion signal can be buffered within a memory (for example, memory 210 in FIG. 2) of the user wearable device(s) 108 for a predetermined time period, and the optical signal and the motion signal can then be provided to other processors for the processing of these signals (for example, processing circuitry 302 of communication device 104 in FIG. 3 or the circuitry of data analysis device(s) 114). As such, power consumption of the user wearable device(s) 108 may be conserved or optimized. Alternatively, in some implementations, processing circuitry 202 of a user wearable device 108 may be used for processing of the optical pulse signal and the motion signal captured by the user wearable device 108.

Signal collection or acquisition from an optical sensor at a 12-50 Hz sampling frequency may be used, especially in optimal conditions such as the general absence of user motion combined with low-levels of perfusion and low ambient light interference. Various conditions can affect the sampling rate considered optimal, but one of the most impactful conditions is the motion of a user wearing the device 108.

Signal processing challenges caused by user motion may be overcome by adjusting various parameters relating to signal acquisition. For example, optical sensor performance can be adjusted when activity is detected by a motion sensor (e.g., a three-axis accelerometer). In some implementations, if motion above a specific threshold is detected, any or all of the following acquisition parameters of an optical sensor can be adjusted to overcome the level of noise and to improve the accuracy of health characteristic determination: (i) sampling frequency, (ii) LED power, and/or (iii) pulses per sample. Conversely, in some implementations, if motion below a specific threshold is detected, then each of these acquisition parameters may be adjusted to maintain a specific level of performance and measurement precision, while also conserving power.

In the general absence of user motion, a sampling frequency of approximately 20 Hz may be appropriate but, in more challenging environments, sampling can be increased to 100 or 200 Hz or, if necessary, up to 1000 Hz or more to ensure that signals are received that are useful for the analysis of user health characteristics. The use of other sampling frequencies is also contemplated.

Various health characteristics of a user may be determined utilizing signals from the sensors discussed herein. As one example, sensors associated with a user wearable device, such as ae watch, may be utilized to determine a user's heart rate, pulse rate variability (PRV) or heart rate variability (HRV). Heart rate is typically described as the number of heart beats per minute, while HRV and PRV both refer to the variability of the time intervals between beats. HRV typically refers to variability measurements based on electrocardiography and can be derived from R-R intervals in the standard PQRS waveform. An HRV determination may utilize an ECG sensor on a user that may communicate with wearable device 108. PRV, on the other hand, typically refers to variability determinations based on sensors placed proximal to peripheral arteries, such as optical sensor(s) on a user's wrist that provide a peripheral pulse waveform absent of the morphology information seen in an ECG signal.

User health characteristics may be determined through signal analysis performed on user wearable device 108 or other components of system 100 such as communication device 102 or data analysis device 114, or the analysis may be performed on more than one component of system 100.

In some implementations, the received sensor signal can be an ECG signal, and the time at which each heartbeat has occurred can be determined, for example, from each R spike in the ECG waveform. Alternatively, the time at which each heartbeat has occurred may be determined from a PPG-signal. In one exemplary implementation, heartbeat times from a PPG-signal may be determined utilizing maximum points of a PPG gradient plot (see, e.g., FIG. 5). Improved resolution for such determinations may be obtained through a variety of methods, for example, spline interpolation, which is further discussed in detail below.

After received signals are analyzed, and precise heartbeat times have been determined (for example, over a sample time of 10 seconds), a heart rate in beats per minute can be determined.

Figure 4:
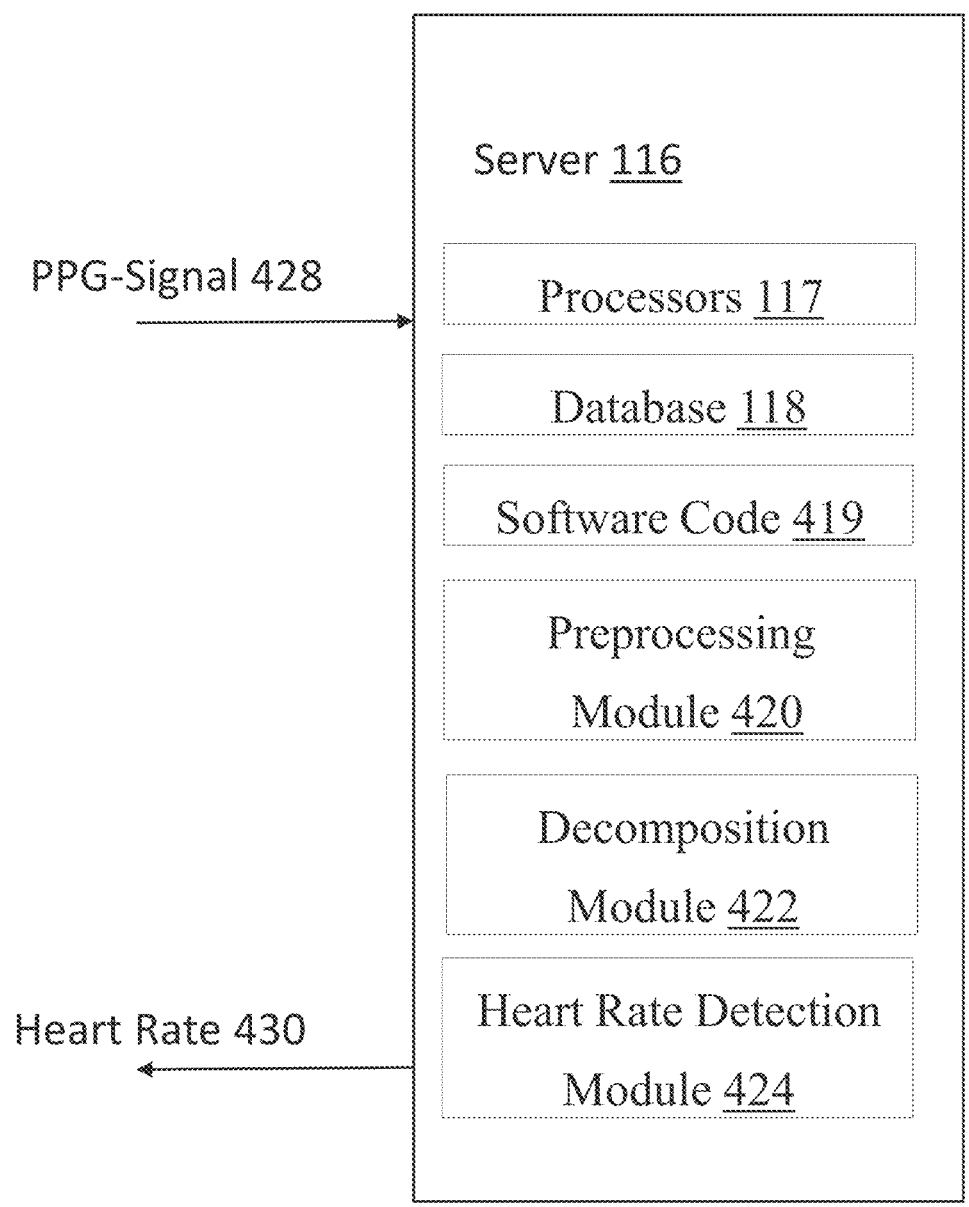
FIG. 4 illustrates an implementation of a server in accordance with certain aspects of the present disclosure.

Referring now to FIG. 4 in conjunction with FIG. 1, FIG. 4 illustrates an exemplary implementation of server 116 of FIG. 1. As shown in FIG. 4, server 116 includes processors 117, database 118, software code 419, preprocessing module 420, decomposition module 422, and heart rate detection module 424. As further shown in FIG. 4, server 116 may be configured to receive PPG-signal 428 and transmit heart rate 430 through network 120 to any of the components of system 100. As noted above, the concepts described herein may be implemented on server 116, wearable device 108, communication device 106, other elements of system 100, or combinations thereof.

In other exemplary implementations, module components of server 117 (modules 420, 422, 424) may be implemented in hardware (including, for example, FPGAs and ASICs), firmware, software, and/or combinations thereof. As used herein, the term "module" is not meant as limiting to a specific physical form. Based on the particular application, modules can be implemented as firmware, software, hardware, and/or combinations of these. In an exemplary implementation, the modules may be implemented as dedicated circuitry (e.g., part of an ASIC). Doing so achieves lower power consumption with increased speed. In another exemplary implementation, the modules may be implemented as software, which runs on digital signal processors and/or general-purpose processors. Various combinations may be implemented. Furthermore, different modules can share common components or be implemented by the same components. There may or may not be a clear boundary between each module component. Finally, the methods described herein do not necessarily need to be implemented by modules at all. The modular structures described herein are provided simply as potential implementations and examples to facilitate the description.

Depending on the form of the modules, the "communication" between modules may also take different forms. Dedicated circuitry can be coupled to each other by hardwiring or by accessing a common register or memory location, for example. Software "communication" can occur by any number of ways to pass information between modules (or between software and hardware, if that is the case). The term "in communication" is meant to include all of these and is not meant to be limited to a hardwired permanent connection between two components. In addition, there may be intervening elements. For example, when two elements are described as being "in communication", this does not imply that the elements are directly coupled to each other nor does it preclude the use of other elements between the two.

In an exemplary implementation, server 116 may be configured for receiving, by processors 417, photoplethysmographic (PPG) signal 428 communicated by a PPG sensor of wearable device 108 worn by a subject. Server 116 may also be configured for processing at least a portion of PPG-signal 428 through frequency band filters to create band outputs corresponding to heartbeat interval ranges. Sever 116 may be further configured for utilizing an indicated band output among the band outputs to determine a first heartbeat and a second heartbeat. In addition, server 116 may be configured for determining heart rate 430 based on at least the first heartbeat and the second heartbeat and causing heart rate 430 to be transmitted to at least wearable device 108.

In an exemplary implementation, after receiving PPG-signal 428, processor 117 may be configured to execute software code 419 in order to detect the presence of noise in PPG-signal 428 and carry out the exemplary implementations described herein. PPG-signal 428 may include a raw signal that may or may not have noise and artifact. By detecting the presence of noise in PPG-signal 428, redundant or unnecessary noise-removal operations may be avoided, thereby achieving faster, more efficient heart rate determinations.

In an exemplary implementation, detecting the presence of noise and artifact may include determining an input instantaneous-amplitude estimate of PPG-signal 428 and forming a time-smoothed version of PPG-signal 428. The instantaneous-peak-amplitude of the dominant component of PPG-signal 428 tends to be stable from heartbeat-to-heartbeat when the signal is free of noise. However, in the presence of noise, the instantaneous amplitude tends to fluctuate significantly. Accordingly, large deviations of the time-smoothed version of PPG-signal 428 may correspond to bursts of noise in PPG-signal 428.

In an exemplary implementation, processor 117 may be configured to detect large instantaneous amplitude deviations of the time-smoothed version of PPG-signal 428. When such instantaneous amplitude deviations exceed a predetermined amount, processor 117 may be configured to determine that noise and artifact are present in PPG-Signal 428.

In another exemplary implementation, when instantaneous amplitude deviations of the time-smoothed PPG-signal 428 are less than a predetermined amount, processor 117 may be configured to determine that noise and artifact are not present in PPG-Signal 428. When PPG-signal 428 is deemed to be free of noise, an exemplary implementation may include not performing preprocessing of PPG-signal 428 for noise removal, as discussed further below.

In yet another exemplary implementation, the instantaneous amplitude of PPG-Signal 428 is compared to a moving average of the instantaneous amplitude. For example, a moving average over 30 seconds of PPG-signal 428. If the instantaneous amplitude is greater than the moving average by predetermined multiplicative factor, the portion of PPG-signal 428 is flagged for noise. In one exemplary implementation the predetermined multiplicative factor can be a factor of 1.5. In other exemplary implementations, the predetermined multiplicative factor may be greater than 1.5 and/or less than 2.

In one exemplary implementation, upon detected large instantaneous amplitude deviations as discussed above, in order to ensure complete coverage of a noisy portion of PPG-signal 428, preprocessing module 420 may be configured to extend the duration of PPG-signal 428 that has been flagged for noise.

While utilizing the time-smoothed version of PPG-signal 428 for determining instantaneous amplitude deviations of PPG-signal 428 is especially well suited for detecting the presence of noise, other methods of determining the presence of noise in PPG-signal 428 may be utilized without diverting from the scope and spirit of the exemplary implementations described herein.

After processing PPG-signal 428 for noise detection as described above, server 116, via preprocessing module 420, may be configured to perform pre-processing of PPG-signal 428.

In an exemplary implementation, preprocessing module 420 may be configured to receive PPG-signal 428 and perform preprocessing of PPG-signal 428. In one exemplary implementation, preprocessing of PPG-signal 428 may include removing high-frequency noise and low-frequency artifact. Preprocessing may also include removing gross end effects including noise pedestal, baseline wander, and DC offset in PPG-signal 428.

In one exemplary implementation, processing PPG-signal 428 by preprocessing module 420 may include first removing gross end effects due to large slowly time-varying DC noise pedestal inherent in PPG-signal 428. This may be achieved by implementing basic straight-line de-trending techniques. Basic straight-line de-trending may function to mitigate end effects of PPG-signal 428 due to large DC offset occurring at the ends of raw input signals, i.e., occurring at the ends of a portion of PPG-signal 428.

In one exemplary implementation, removing gross end effect may further include removing pedestal at each end of at least a portion of the PPG-signal 428. In an exemplary implementation, pedestal at each end of at least a portion of PPG-signal 428 may be estimated by taking the mean of PPG-signal 428 signal vector over nominally 2 seconds from each end. A trend-line may then be implemented from the first sample time to the end sample time of PPG-signal 428. The trend-line thus passes through the mean values corresponding to the first sample time and the end sample time. Subtracting the values resulting from this trend-line computation from the raw input signal, i.e., PPG-signal 428, results in the de-trended output signal, i.e., a filtered PPG-signal 428.

In an exemplary implementation, removing large artifacts may include implementing high-pass and low-pass filtering to suppress large artifacts. High-pass and low-pass filtering may include implementing cascaded low-pass and high-pass filters to suppress high and low frequency artifacts, respectively. In another exemplary implementation, the high-pass filter may be implemented by subtracting the delay centered output of an internal low-pass filter from the input of the low-pass filter.

In an exemplary implementation, preprocessing filtering may be implemented utilizing linear-phase filters in order to preserve the primary morphological features of the underlying PPG-signal 428 and to align time delays from input to output at all frequencies. In another exemplary implementation, preprocessing filtering may include utilizing cascades of boxcar filters. In one exemplary implementation, preprocessing PPG-signal 428 may include utilizing a bandpass filter with corner frequencies at band pass high 0.5 hertz and bandpass low 10 hertz.

In another exemplary implementation, PPG-signal 428 may undergo further input processing to remove large artifacts existing outside the desired bandwidths of PPG-signal 428. In yet another exemplary implementation, other filter protocols for removing noise and artifact may utilized, e.g., blind source separation utilizing independent component analysis for uncovering independent source signal components and deducing linear mixtures of underlying sources. Other noise removing filtering processes may be implemented without diverting from the scope and spirit of the present implementations described herein, and have been fully contemplated.

In one exemplary implementation, in order to remove intrinsic latency delay associated with preprocessing PPG-signal 428, the output signal of preprocessing module 420, i.e., filtered PPG-signal 428, may be the same length as the input signal, i.e., raw PPG-signal 428, and aligned in time as well. In another exemplary implementation, the output signal may not be the same length as the input signal the filtered PPG-signal may not be time aligned. While the preprocessing methods described above are especially well suited for implementing the exemplary implementations described herein, other methods of separating time-series signals into composite sub-components using a signal reference may be implemented without diverting from the scope and spirit of the present implementations, and have been fully contemplated herein.

As used herein, the filtered PPG-signal 428 may be referred to as simply PPG-signal 428. Any reference to filtered PPG-signal 428 or simply PPG-signal 428 may thus refer to a filtered or non-filtered PPG-signal and should not be construed as limiting the PPG-signal 428 to a particular implementation.

In an exemplary implementation, after performing the preprocessing of PPG-signal 428, preprocessing module 420 may be configured to communicate filtered PPG-signal 428 to decomposition module 422. Decomposition module 422 may then perform operations on the filtered PPG-signal 428 in preparation for detecting heartbeats and determining heart rate.

Decomposition module 422 may be configured to decompose PPG-signal 428. Decomposition may be implemented in linear-phase to preserve morphology characteristics of PPG-signal 428. Decomposing PPG-signal 428 may also include separating PPG-signal 428 into a series of sub-signals that in aggregate substantially comprise PPG-signal 428 (substantially meaning the difference may be negligible). Accordingly, decomposition module 422 may be utilized for decomposing PPG-signal 428 by separating, from PPG-signal 428, a set of PPG sub-signals.

Decomposing PPG-signal 428 may include processing at least a portion of PPG-signal 428 through frequency band filters. In one exemplary implementation, the frequency bands filters may correspond to bandwidth ranges of 0.55-1.37 hertz, 0.78-2.33 hertz, and 1.26-4.25 hertz, respectively. In another exemplary implementation, the frequency band filters are designed to be less than one octave wide. Stated another way, the bandwidth of the frequency band filters are chosen to prevent inclusion of two or more successive harmonics of the PPG-signal. In this manner, only the first harmonic of input signals substantially appears at the output for locally periodic input signals within the frequency band range. Consequently, at the time surrounding each heartbeat, the frequency band filter having a passband (i.e., bandwidth range) that covers the local fundamental pulse rate will be excited by the greatest amount, and therefore, will exhibit the greatest amplitude at the output.

In addition to having the largest amplitude, the largest amplitude output band of the frequency band filters will also exhibit the greatest purity of the local sinusoid since only the fundamental harmonic appears at the output of the frequency band filters. Accordingly, the frequency band output having the largest amplitude corresponds to the fundamental frequency of the input signal (i.e., the main component of the input signal).

In an exemplary implementation, frequency band filters may include a wavelet bank utilizing successively increasing semi-dyadic cascade of low-pass/high-pass separations. In another exemplary implementation, decomposition module 422 may be configured for decomposing PPG-signal 428 through the wavelet bank and producing an output. Wavelet bank outputs (i.e., frequency band outputs), may be delay-aligned and centered in time upon the input signal, PPG-signal 428. In this manner, the intrinsic delay due to latency associated with the wavelet bank may be removed in order to ensure accurate heart rate determinations. Accordingly, processing at least a portion of PPG-signal 428 through frequency band filters may include creating band outputs.

In one exemplary implementation, decomposing PPG-signal 428 may include processing PPG-signal 428 through frequency band filters to create band outputs corresponding to a plurality of heartbeat interval ranges. Heartbeat interval ranges may correspond to frequency ranges associated with expected heart rates of the subject. For example, heartbeat interval ranges may correspond to a normal range, a tachycardia range, and a bradycardia range. In other implementations, the heartbeat interval ranges may correspond to different ranges that may be useful in separating PPG-signal 428 into frequency ranges corresponding to likely heart rate ranges of the user.

Further signal processing techniques may be implemented for ensuring that the frequency band filters produce outputs that are robust and free of signal degradation complexities. For example, in one exemplary implementation, utilizing frequency band filters may include applying an input vector gain between each of the successive cascades in order to address signal attenuation and other signal degradation issues. Various other approaches may be utilized for filtering PPG-signal 428 including: matched filters, second order derivatives, nonlinear timescale decomposition, adaptive filtering, dynamic time warping, artificial neural networks, or hidden Markov models.

Decomposition module 422 may be configured to communicate decomposed portions of PPG-signal 428 (e.g., frequency band outputs) to heart rate detection module 424. In an exemplary implementation, heart rate detection module 424 may be configured for tracking each of the communicated frequency band outputs and determining, by comparison, which of the frequency band outputs has the largest amplitude. The largest amplitude band output may be indicative of the user's heart rate being within that band and that band may thus be used to determine heartbeats. Thus, heart rate detection module 424 may be configured for determining amplitudes for the band outputs and determining the largest amplitude band output among the band outputs, where identification of an "indicated" band output corresponds to the largest amplitude band output. The indicated band output may then be utilized to determine a first heartbeat, a second heartbeat, and a heart rate from PPG-signal 428, as discussed further below.

In another implementation, heart rate detection module 424 may be configured to utilize more than one frequency band output. For example, heartrate detection module 424 may generate a running estimate of the amplitudes of the frequency band outputs and may perform further processing on the band outputs with the two highest amplitudes. This method may provide faster heart rate determination/tracking in cases where heart rates are changing rapidly beat-to-beat and perhaps moving from one frequency band to another. Accordingly, in an exemplary implementation, in addition to determining the largest amplitude band output, analysis module 424 may be configured for determining a second largest amplitude band output and utilizing the second largest amplitude band output to determine an "anticipated" heartbeat. The "anticipated" heartbeat may potentially be the appropriate heartbeat to analyze if the heart rate has moved into the new frequency band. Heart rate detection module 424 may thus be further configured for utilizing the anticipated heartbeat in determining heart rate 430 when the indicated band output changes, to provide faster heart rate tracking and transmission to wearable device 108.

For example, in one exemplary implementation, the largest amplitude band may correspond to the normal band range, while the second largest amplitude band output may correspond to the tachycardia heart rate range. Tracking both band outputs may then provide for faster tracking in the case where heart rate is changing rapidly, as can occur with certain arrhythmias such as atrial fibrillation.

In one implementation, heart rate detection module 424 may be configured to "qualify" the second largest amplitude band for further processing (e.g., the determining of anticipated heartbeats). Qualifying the second largest amplitude band output may include, for example, determining if the second largest amplitude band output is a sufficient fraction of the largest amplitude band output. In the case where the second largest amplitude output is a sufficiently small fraction (e.g., <0.85), heart rate detection module 424 may forgo further processing of the second largest amplitude output band and the determination of anticipated heartbeats in that band.

Heart rate detection module 424 may be further configured to utilize the band outputs described above in determining heartbeats (or, similarly, anticipated heartbeats). Determining heartbeats in this sense generally refers to determining the times at which heartbeats take place. Such times may then be used in determining heart rates.

Figure 5:
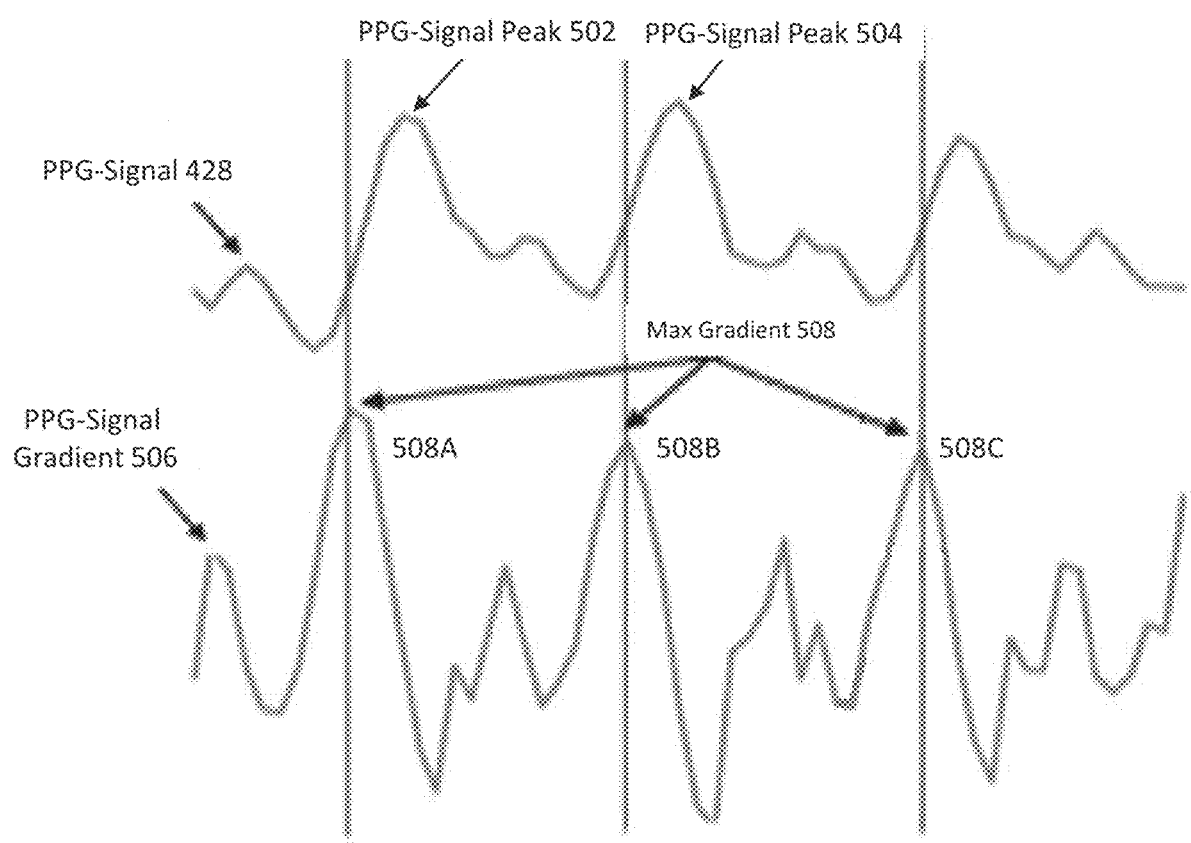
FIG. 5 illustrates an exemplary PPG-signal and corresponding PPG-signal gradient in accordance with certain aspects of the present disclosure.

One technique for determining heartbeats contemplated by the present disclosure utilizes the rate of change of the PPG-signal (also referred to as the PPG-signal gradient). FIG. 5 depicts an exemplary PPG-signal 428 (having a first PPG-signal peak 502 and a second PPG-signal peak 504), and a PPG-signal gradient 506 (having maximum gradients 508A, 508B, and 508C).

In one exemplary implementation, determining the first heartbeat and a second heartbeat may include determining the first heartbeat and second heartbeat from maximum gradients 508 of PPG-signal 526.

As shown in FIG. 5, maximum gradients 508 depict the locations of the fastest incline of the PPG-signal 528, i.e., the maximum values of PPG-signal gradient 506. These locations can then be deemed heartbeats (i.e., the times at which heartbeats occur). The heartbeats may then be utilized to determine heart rate.

Sampling rate limitations inherent in the acquisition of PPG-Signal 428 can result in the PPG-signal peaks (502 and 504) and gradient peaks (508A,B,C) shown in FIG. 5 appearing to be in a location different from the actual peak (as would be depicted should there be no limit on sampling rate).

Figure 6:
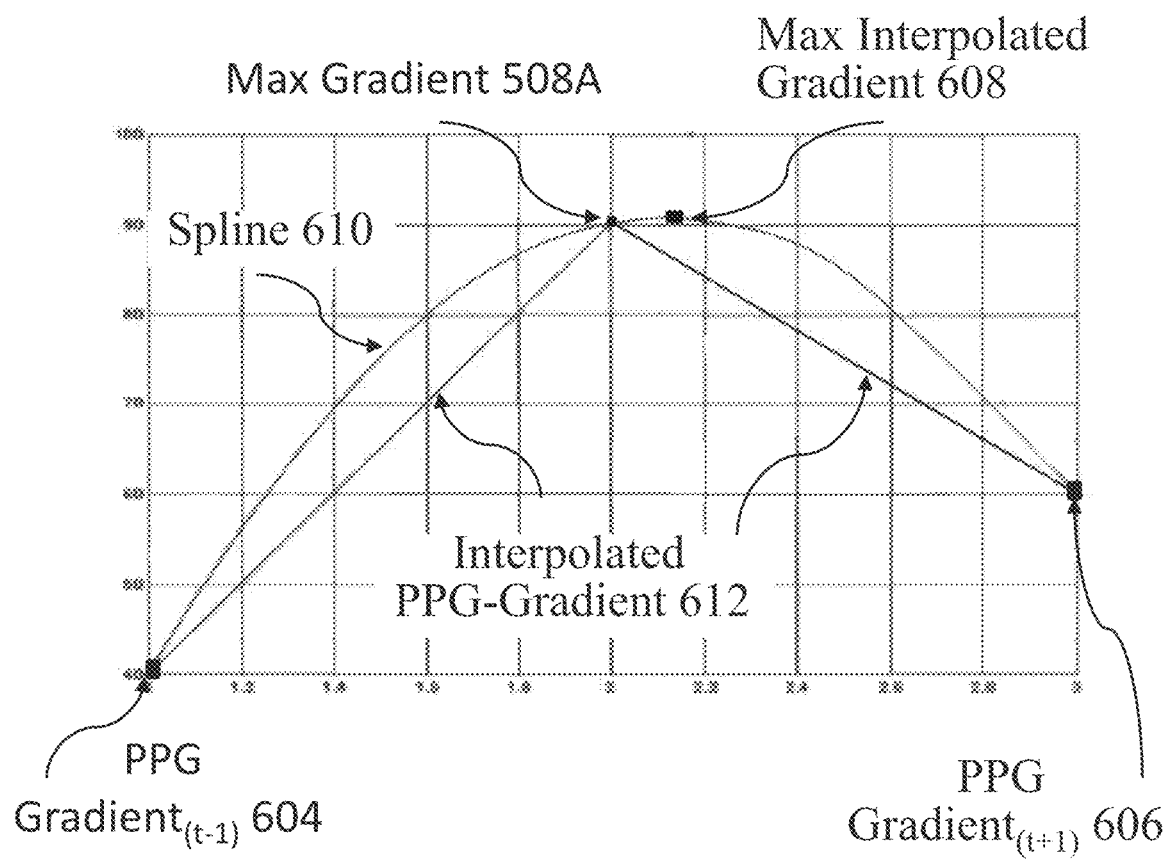
FIG. 6 illustrates an exemplary implementation of a heartbeat determination method.

In order to overcome the sampling resolution limitations inherent in the PPG sensing process and to increase the accuracy of heart rate determinations, heart rate detection module 424 may be configured to utilize various methods for determining a more accurate gradient peak. One such method may be explained with reference to FIG. 6. FIG. 6 depicts maximum gradient point 508A from FIG. 5, along with two other gradient curve points (depicted as PPG gradient$_{T-1}$ 604 and PPG gradient$_{T+1}$ 606) that can be used with, e.g., a spline interpolation 610 to determine a more accurate gradient peak 608. Accordingly, heart rate detection module 424 may be configured for determining a heartbeat utilizing maximum gradient 508A, at least two other data points from the gradient of PPG-signal 428, and a mathematical method.

In an exemplary implementation, the mathematical model may comprise spline interpolation. Also, the at least two other points may include samples of PPG-signal gradient 506 at immediate intervals before and after maximum gradient 508, i.e., PPG gradient$_{T-1}$ 604 and PPG gradient$_{T+1}$ 606. As further shown in FIG. 6, the more accurate gradient peak 608 may be determined by utilizing the three points (gradient$_{T-1}$ 604, PPG gradient$_{T+1}$ 606, and maximum gradient 508A) and spline interpolation, or another method, thus increasing the accuracy of heart rate determinations.

In one implementation, a state based sequence detector may be utilized to determine the two other data points from the gradient of the PPG-signal and to implement the mathematical method. While a state based sequence detector is especially well-suited for implementing the methods described herein for determining the other data points and implementing the mathematical method, other implementations may be utilized without diverting from the scope and spirit of the implementations described herein.

The processes described above can be repeated for other intervals containing a heartbeat in PPG-signal 428 and the time intervals between heartbeats allow heart rate 430 to be determined. Accordingly, heart rate detection module 424 may be configured to utilize the exemplary processes described above for determining heart rate 430 based on at least a first heartbeat and a second heartbeat and to cause heart rate 430 to be transmitted to at least wearable device 108 and/or any other component of system 100.

In an alternative heartbeat determination method, PPG-signal peaks are utilized instead of gradient peaks. For example, heart rate detection module 424 may configured to utilize frequency band output signals for determining a first PPG-signal peak 502 and second PPG-signal peak 504 from at least a portion of PPG-signal 428 and then determining a first heartbeat and a second heartbeat from the first PPG-signal peak 502 and the second PPG-signal peak 504. For example, the heartbeat may be considered to be at the location of the PPG-signal peak, or at an offset from the peak. The heart rate detection module 424 may then determine heart rate 430 based on the first heartbeat and the second heartbeat.

In order to overcome the sampling resolution limitations inherent in the PPG sensing process and to increase the accuracy of heart rate determinations, heart rate detection module 424 may be configured to utilize various methods for determining more accurate PPG-signal peaks. One such method may be explained as similar to the process described above with reference to FIG. 6. In a similar vein, heart rate detection module 424 may be configured for determining a heartbeat utilizing PPG-signal peak 502, at least two other data points from PPG-signal 428, and a mathematical method.

In an exemplary implementation, the mathematical model may comprise spline interpolation, but other methods may be utilized, as noted above.

The at least two other points from the PPG-signal 428 may, in one implementation, include a positive-going zero crossing and a negative-going zero crossing nearest PPG-signal peak 502. Such PPG-signal zero-crossings may be determined using a zero-crossing narrowband filter. The zero-crossing narrowband filter may be included in the frequency band filters as described above. The narrowband nature of the zero-crossing filter tends to produce output waveforms that are, on a time local per cycle basis, close to sinusoidal in waveform. Because these waveforms are substantially sinusoidal, they produce zero-crossings that are well behaved and reliable. The zero-crossing narrowband component of PPG-signal 428, is time aligned with PPG-signal 428. In this manner, the zero-crossings function to bracket PPG-signal peaks 502,504 in PPG-signal 428. A more accurate PPG-signal peak may then be determined utilizing the zero crossings with the original PPG-signal peak and a mathematical method, as described above.

In one implementation, a state based sequence detector may be utilized to determine the two other data points from the PPG-signal and to implement the mathematical method. While a state based sequence detector is especially well-suited for implementing the methods described herein for determining the other data points and implementing the mathematical method, other implementations may be utilized without diverting from the scope and spirit of the implementations described herein.

As discussed, the PPG-signal peaks, or the more accurate PPG-signal peaks, may be used to identify heartbeats at the locations of the peaks, or at some offset therefrom. These heartbeats may then be used to determine a user's heart rate, which may be, for example transmitted to and displayed on wearable device 108 or any other component of system 100.

As described throughout the present disclosure, a user can monitor their heart activity with a wearable device (e.g., a smartwatch including a PPG sensor). System 100 can then be configured to alert the user, a healthcare provider, etc., when an irregular heart rhythm type is detected through analysis of the received heart data. In one example, an alert can be provided when atrial fibrillation (AF) is detected.

Figure 7:
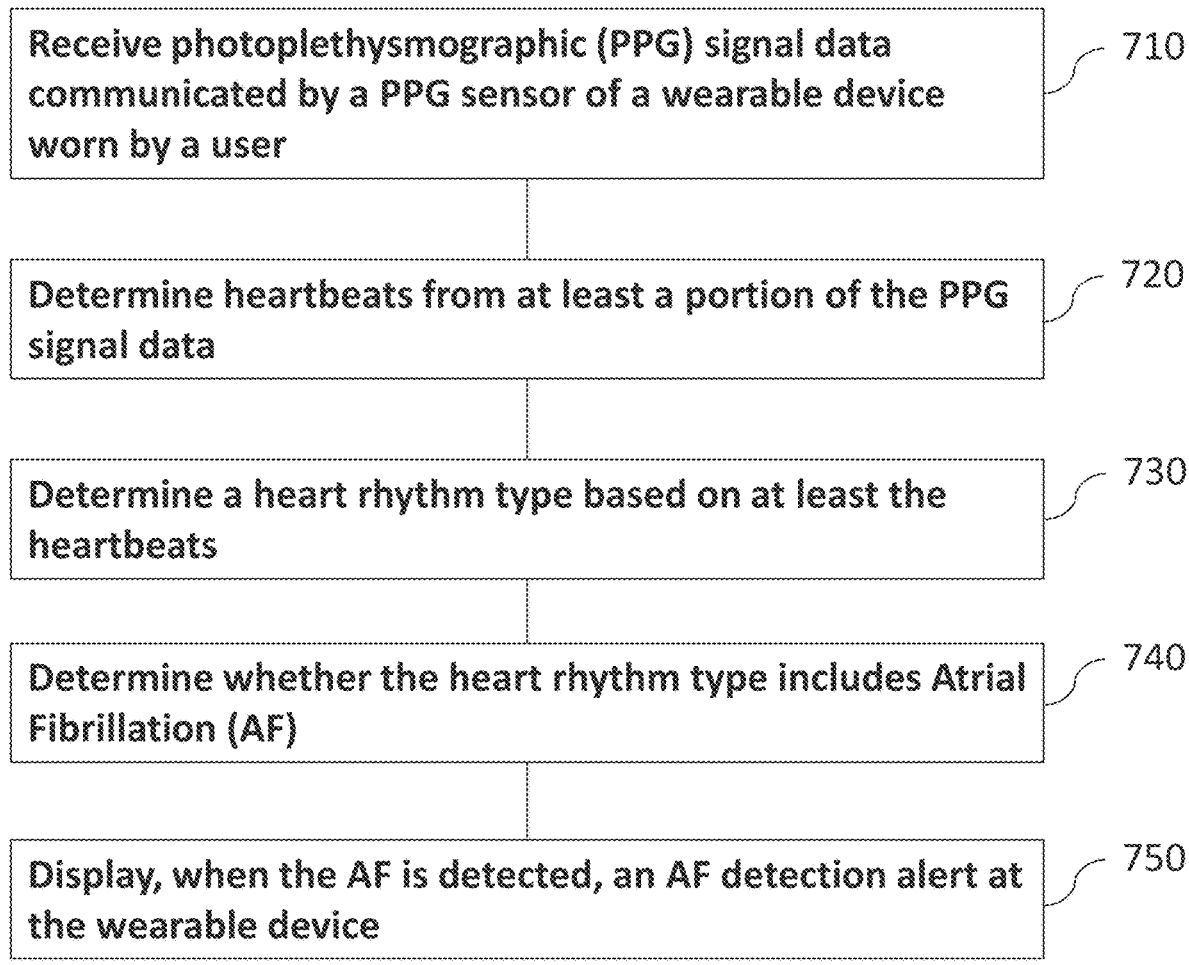
FIG. 7 is a diagram illustrating an exemplary process for determining the presence of atrial fibrillation in accordance with certain aspects of the present disclosure.

FIG. 7 is a diagram illustrating a basic exemplary process for determining the presence of atrial fibrillation in accordance with certain aspects of the present disclosure. This determination can be performed by executing one or more algorithms that analyze PPG sensor data. In some implementations, a computer can, at 710, receive photoplethysmographic (PPG) signal data communicated by a PPG sensor of a wearable device worn by a user. As discussed herein, the algorithm can, at 720, determine heartbeats from at least a portion of the PPG signal data and can, at 730, determine a heart rhythm type based on at least the heartbeats. As discussed in detail below, the system can also, at 740, determine whether the heart rhythm type includes Atrial Fibrillation (AF). The operations can also include, at 750, displaying, when AF is detected, an AF detection alert at the wearable device. Details of exemplary algorithms and analysis to detect and identify various heart rhythm types (e.g., normal sinus rhythm or atrial fibrillation (AF)) are discussed further below.

Certain exemplary systems, methods and software contemplated herein can analyze and detect heart rhythms utilizing a Poincaré space, a two-dimensional space that may be formed and visualized by plotting a current heartbeat interval along one axis and the preceding interval along the other axis. For normal heart rhythms, such points tend to be distributed densely and narrowly around the local average interval. For AF, such points tend to be distributed more widely, with large jumps in intervals occurring with successive heartbeats.

In certain exemplary methods, heart rhythm determination can utilize metrics based upon this space. For example, a metric based on occupancy of the space (e.g., how much of the space is taken up by the plotted points) and/or a metric based on the median of the distances measured from point to point. Other metrics may also be utilized, for example a metric based on the variability of heartbeat intervals. Such metrics can be computed over a moving window of contiguous heartbeats (e.g., 48 heartbeats), to balance a local time focus with the stability of the metrics. These metrics can be computed and updated with each heartbeat, compared against individual thresholds, and then a particular pattern can be declared if the metrics exceed certain thresholds. To improve the accuracy of certain heart rhythm determinations, a particular heart rhythm pattern may only be formally declared when a sufficient number of the patterns are declared over a local group of heartbeats.

Figure 8:
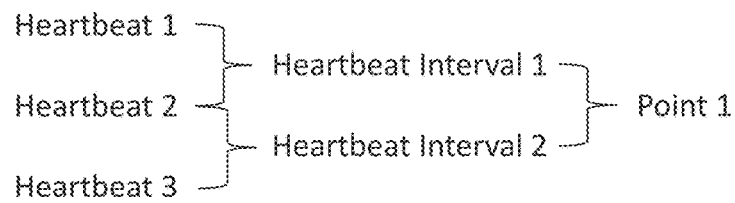
FIG. 8 is a diagram illustrating an exemplary scatter plot representative of a normal heart rhythm in accordance with certain aspects of the present disclosure.
Figure 8:
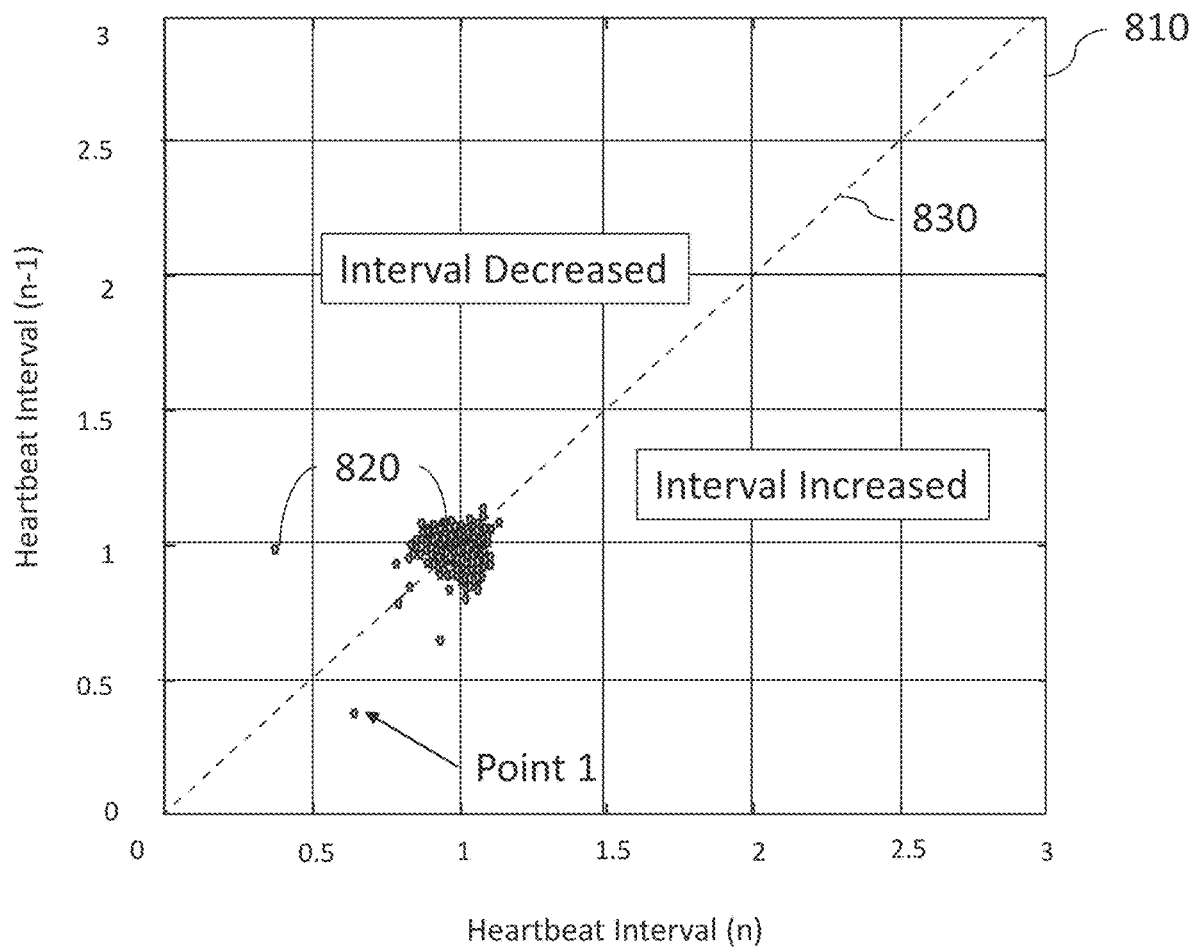

FIG. 8 is a diagram illustrating an exemplary scatter plot 810 representative of a normal heart rhythm in accordance with certain aspects of the present disclosure. Scatter plot 810 contains points 820 that are determined to represent heartbeat interval changes over a period of time (or number of heartbeats, heartbeat intervals, etc.). Points 820 can represent a change between two adjacent (or local) heartbeat intervals. As used herein, "adjacent" means that one heartbeat interval can be either preceding or subsequent the other heartbeat interval.

Figure 9:
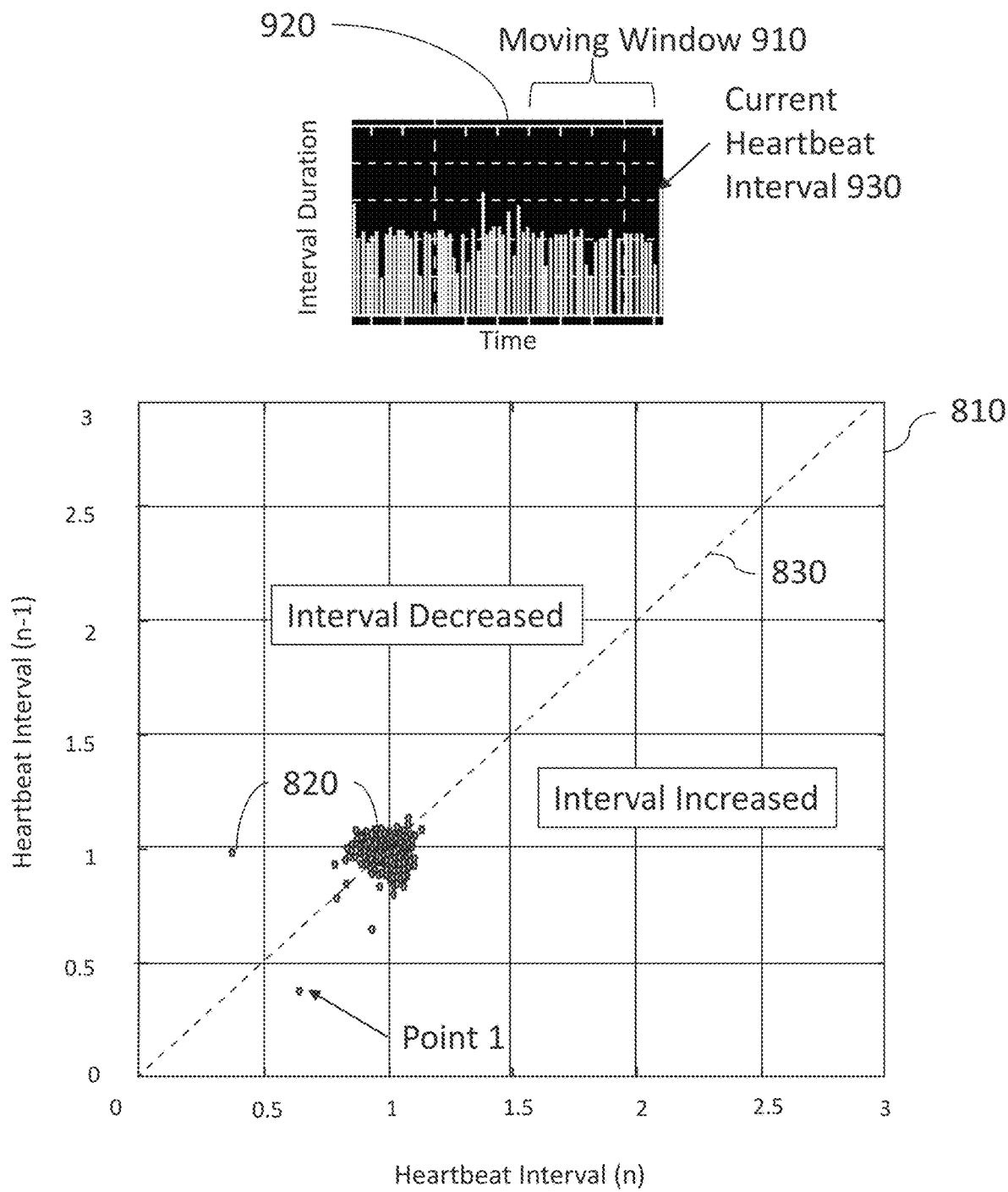
FIG. 9 is a diagram illustrating an exemplary moving window used in the generation of a scatter plot in accordance with certain aspects of the present disclosure.
Figure 10:
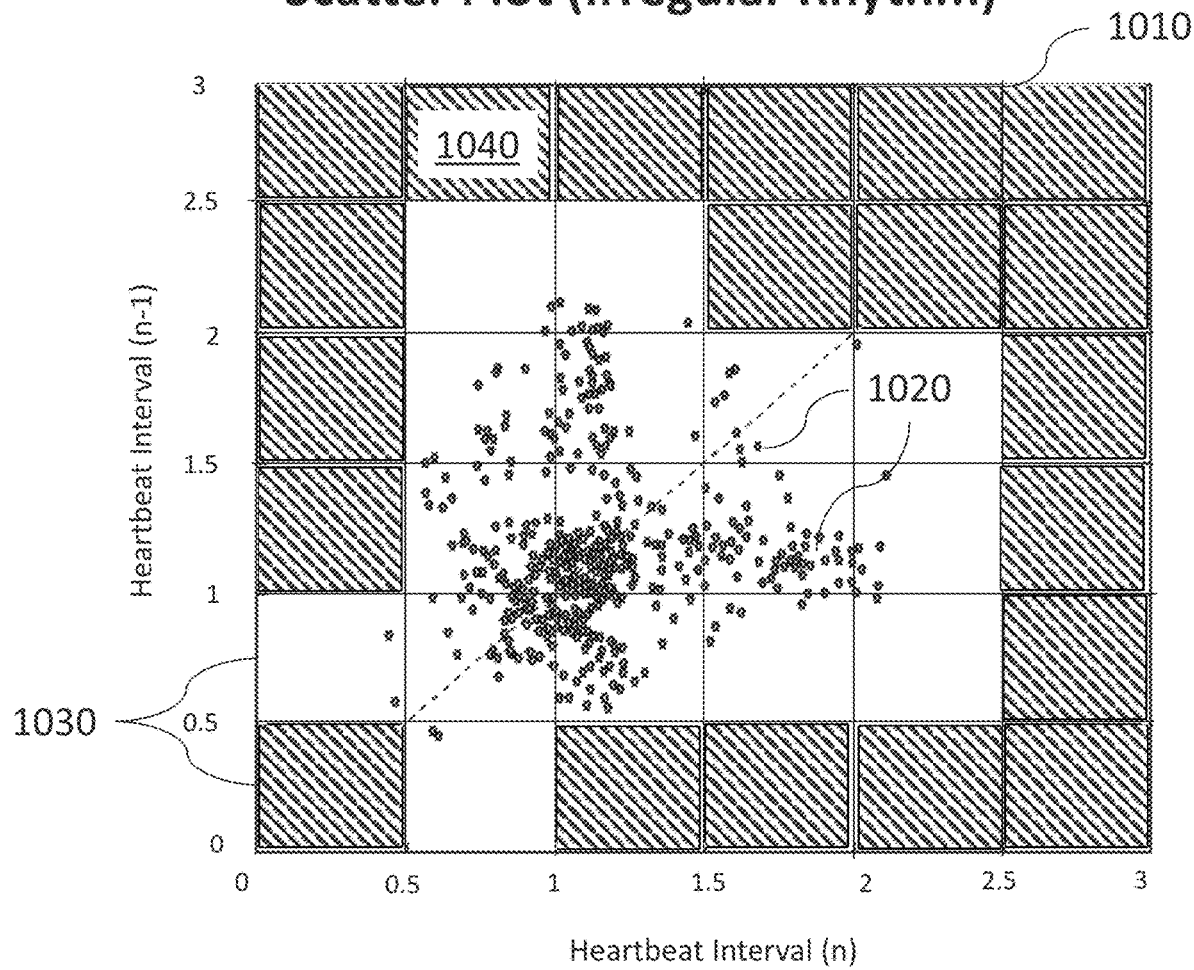
FIG. 10 is a diagram illustrating an exemplary method for determination of an occupancy metric from a scatter plot representative of an irregular heart rhythm in accordance with certain aspects of the present disclosure.
Figure 11:
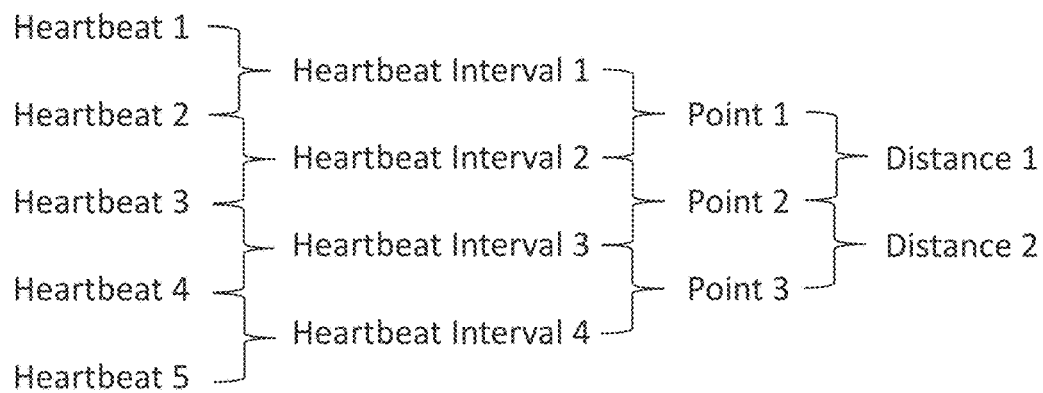
FIG. 11 is a diagram illustrating an exemplary method for determination of a distance metric from a scatter plot representative of an irregular heart rhythm in accordance with certain aspects of the present disclosure.
Figure 11:
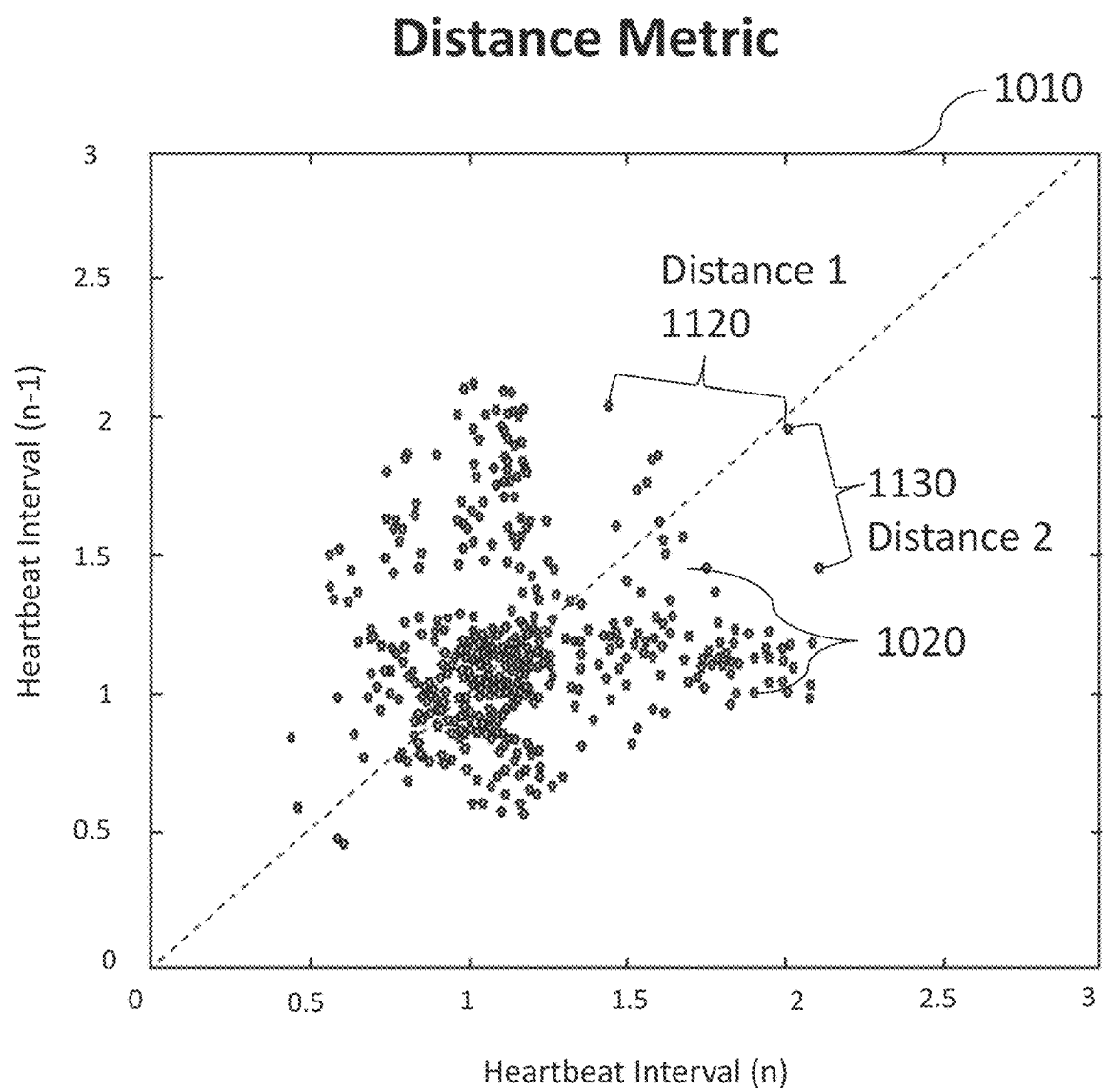

While the description of such points 820 is made with reference to FIG. 8, it is understood that the description applies equally to references to similar points in the present disclosure (e.g., as in FIGS. 9, 10, and 11). Determination of an exemplary point is further illustrated by the top portion of FIG. 8, where Heartbeat 1 and Heartbeat 2 can define Heartbeat Interval 1. Similarly, Heartbeat 2 and Heartbeat 3 can define Heartbeat Interval 2, and together, Heartbeat Interval 1 and Heartbeat Interval 2 can provide the X and Y coordinates for Point 1.

Points 820 can be implemented, for example, as values stored in computer memory in the form of variables, arrays, vectors, matrices, objects, or other such data structures. Points 820 can be expressed graphically or merely represented in computer memory. The points can be formatted, for example, to represent an absolute change in heartbeat interval (e.g., 0.5 sec, −0.1 sec, etc.) or a ratio (e.g., 0.9—when one heartbeat interval is 90% of the adjacent heartbeat interval). Other expressions of points 820 that represent heartbeat interval changes over a period of time are also contemplated and considered within the scope of the present disclosure.

In further describing exemplary FIG. 8, the horizontal axis of scatter plot 810 refers to one heartbeat interval (e.g., interval n) and the vertical axis refers to a second interval (e.g., a preceding interval n−1). When a heart exhibits a normal heart rhythm type, points 820 may not change significantly over time. Accordingly, a plot of points 820 for a normal heart rhythm will generally be localized to a limited region (as shown FIG. 8). In the example shown, points 820 have been normalized by the average heartbeat interval (e.g., for a heartbeat interval n being 0.6 sec and heartbeat interval n−1 being 0.4 sec, the point would fall at Point 1 in the example scatter plot). Accordingly, as indicated in FIG. 8, when a heartbeat interval increases, such points 820 will be below the 45 degree line 830. When the heartbeat interval decreases, such points 820 will be above the 45 degree line 830.

FIG. 9 is a diagram illustrating an exemplary moving window 910 based on PPG signal data used in the generation of exemplary scatter plot 810 in accordance with certain aspects of the present disclosure. Points 820 used for determination of a heart rhythm type can be determined for moving window 910 (e.g., the period of time) containing some number of heartbeats or heartbeat intervals, etc. Accordingly, the points used to generate the exemplary scatter plots, and/or the points used to determine the metrics discussed herein can be based on a moving window 910. One exemplary illustration of a moving window 910 is referenced in interval plot 920 in the top portion of FIG. 9. Moving window 910 contains a number of heartbeats or heartbeat intervals, including, in this example, the current heartbeat and current heartbeat interval 930. While discussed with respect to FIGS. 8 and 9, moving window 910 can also be used in the generation of any of the scatter plots or datasets described herein.

Moving window 910 may be designed to contain a predefined number heartbeats prior to and/or including the current heartbeat. For example, in some implementations, moving window 910 can include 50 heartbeats, 100 heartbeats, 192 heartbeats, 500 heartbeats, etc. In some implementations, a specific number of heartbeats can be identified as providing an optimization between recency of heartbeat data and accuracy of the heart rhythm type determination. For example, 48 heartbeats can be one such specific number.

Similarly, in some implementations, moving window 910 can be based on a predefined or optimized time period (e.g., 15 seconds, 30 seconds, one minute, five minutes, etc.). In other implementations, moving window 910 can be based on a predefined number of heartbeat intervals (e.g., 10 heartbeat intervals, 20 heartbeat intervals, 48 heartbeat intervals, 100 heartbeat intervals, etc.), or can be designed to change in scope based on certain factors.

FIG. 10 is a diagram illustrating an exemplary method of determination of an occupancy metric from an exemplary scatter plot 1010 representative of an irregular heart rhythm in accordance with certain aspects of the present disclosure. The computational algorithms described herein can generate quantitative metrics that can be used to accurately determine heart rhythm types, such as AF. Comparing FIG. 10 to FIG. 8 or 9, it can be seen that the distribution of points 1020 in FIG. 10 is larger. Accordingly, in some implementations, the algorithm can determine an occupancy metric based at least partially on an interval scatter analysis. Subsequently, and as discussed in greater detail below, determining the heart rhythm type can further include utilization of the occupancy metric.

As used herein, the term "interval scatter analysis" means an analysis, performed by a computer, of changes in heartbeat intervals. The changes in heartbeat intervals can be expressed or visualized as, for example, points in the scatter plots of FIG. 8, 9, 10, etc. The changes in heartbeat intervals can also be represented in computer memory in the form of arrays, tables, etc. or calculated from heartbeat data. In such implementations, the interval scatter analysis can optionally be performed without plotting points in scatter plots. An interval scatter analysis can include quantifying some characteristic of the distribution of changes in heartbeat interval. For example, as visualized in the exemplary scatter plots. The characteristics (or metrics) can include an occupancy associated with the points in the scatter plots, as described further herein.

As used herein, an "occupancy metric" means a metric (e.g., a number, vector, or some value) that quantifies the distribution of points in a defined space—that is, provides a measure of the degree to which the space is "occupied" by one or more points. The space can be a scatter plot, array, table or graph, etc.

In one exemplary determination of an occupancy metric, scatter plot 1010 of FIG. 10 may be subdivided into a number of areas 1030. Areas 1030 that do not contain any points are shown with shading (e.g., area 1040). In the example of FIG. 10, there are 36 areas 1030 shown. Due to the distribution of points in scatter plot 1010, 16 of areas 1030 contain at least one point 1020. Accordingly, in this example, the occupancy of this distribution of points 1020 is 16/36=0.444. By way of comparison, though not shown, the occupancy metric of the scatter plot 810 in FIG. 8 or 9 would be 6/36=0.166. This exemplary method thus demonstrates that an occupancy metric can be calculated to result in a higher value when there is a greater variation in heartbeat intervals (and thus a higher likelihood of AF). It is understood, however, that occupancy metrics can be calculated and utilized in alternative ways.

While the example illustrated in FIG. 10 is discussed in terms of areas of a scatter plot, computational solutions are contemplated that perform a similar analysis based on, for example, binning, partitioning, sorting, or the like. Some implementations of the current subject matter can include defining bins into which the points may fall. The occupancy metric can be determined by determining a fraction of bins that contain at least one of the points.

As used herein, a "bin" means a section, area, volume or data structure that can potentially include one or more points. For example, a bin, as realized by computer software, can be a particular area in a scatter plot (as shown in the example below), portion of a data structure corresponding to the points, etc. Accordingly, implementations can enable such binning and the like by using arrays, matrices, objects, or other forms of computational data partitioning to represent the heartbeat intervals and areas 1030 illustrated in FIG. 10. For example, an array of points 1020 can be partitioned or binned in computer memory according to where they would fall in a defined area (or range) representing a degree of change between adjacent intervals.

FIG. 11 is a diagram illustrating determination of an exemplary distance metric from an exemplary scatter plot 1010 representative of an irregular heart rhythm in accordance with certain aspects of the present disclosure. Similar to the occupancy metric, an algorithm can determine a distance metric based at least partially on points representing heartbeat interval changes, which may be represented in a scatter plot as shown in FIG. 11. As before, determining the heart rhythm type can further include utilization of the distance metric.

As used herein, a "distance metric" provides a measure of the degree of change in the heartbeat intervals, typically calculated in terms of a "distance" between points representing the change in heartbeat intervals. For example, a distance metric can be based on distances calculated between points in the exemplary scatter plots (e.g., FIG. 11). A large distance metric indicates large changes in heartbeat interval (possibly indicative of an irregular heart rhythm) and a small distance metric indicates small changes in heartbeat interval (possibly indicative of a regular heart rhythm).

In the discussion below regarding the distance metric, the example of FIG. 11 uses the same scatter plot 1010 and points 1020 shown in FIG. 10. Similar to that shown in FIG. 8, the top FIG. 11 also contains an exemplary illustration of what points, intervals, and heartbeats may be included in the determination of a distance metric.

In some implementations, the distance metric can be determined from a median of distances between the points (e.g., points 1020). Similarly, the distance metric could be determined from a mean of distances between the points. In the example of FIG. 11, a first distance (Distance 1) 1120 can be calculated between consecutive points 1120 as shown. Similarly, a second distance (Distance 2) 1130 can be calculated between another two points 1130. Because the points used to calculate the distance metric in this example are consecutive, Distance 2 1130 is calculated with a common point—point 2—with Distance 1 1120. The distance metric may then correspond to the median of any number of such distances, for example any or all points 1020 shown in scatter plot 1010 or the points included within a particular moving window. An interval variability metric may also be determined based on heartbeat intervals that are derived from a number of heartbeats, for example, the heartbeats included in a moving window. In some implementations of the current subject matter, determining the heart rhythm type can further include utilization of such an interval variability metric.

As used herein, an "interval variability metric" represents a measure of variation of heartbeat intervals for some number of heartbeats. In one example, the interval variability metric could be the standard deviation of the examined intervals.

In another example, the interval variability metric may involve examining changes in heartbeat intervals from one heartbeat to the next. For example, an interval defined by a first and second heartbeat (e.g., Interval 1=1000 ms) can be compared to a heartbeat interval defined by a second and third heartbeat (e.g., Interval 2=900 ms). The change from Interval 1 to Interval 2 would then be one hundred milliseconds. Such heartbeat interval changes from heartbeat to heartbeat may then be averaged over a period of time. The interval variability metric then, in one example, can be a median of the absolute changes in heartbeat intervals. This exemplary method can be illustrated with the following equation:

$$\text{Interval Variability Metric} = \text{median}(ABS(\Delta(\text{interval}))) \quad (1)$$

Figure 12:
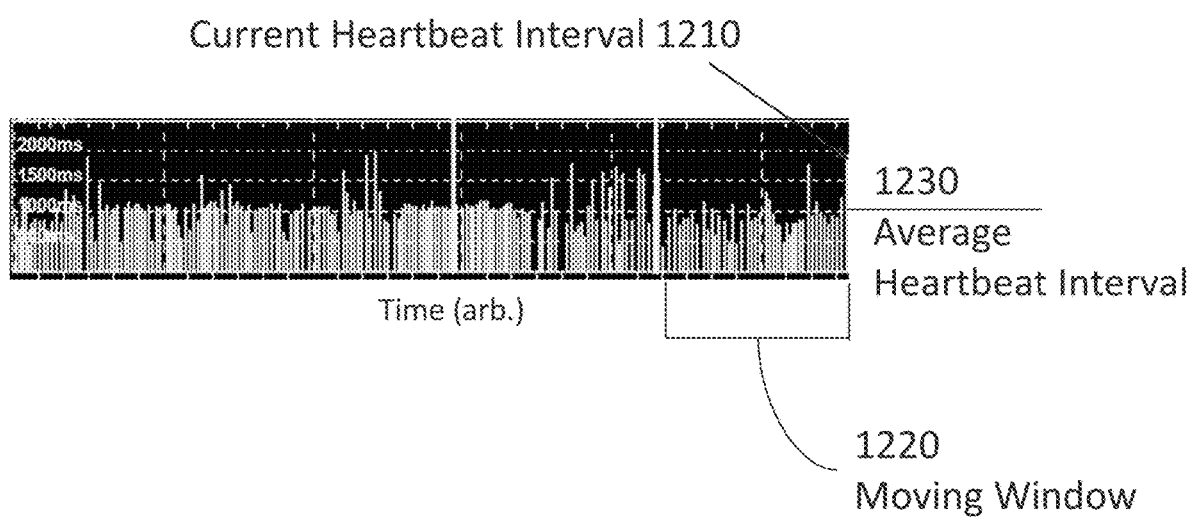
FIG. 12 is a diagram illustrating an exemplary method for determination of an interval variability metric from heartbeat interval data in accordance with certain aspects of the present disclosure.

In another implementation, an interval variability metric may be calculated based at least on a current heartbeat interval 1210 and an average heartbeat interval 1230 (as shown in FIG. 12). The heartbeat intervals can be contained in moving window 1220 (e.g., of 192 beats), or can be any other desired set of intervals. In the exemplary selection of heartbeat intervals shown in FIG. 12, average heartbeat interval 1230 for the moving window 1220 is illustrated by a horizontal line extending from the right side of FIG. 12. In some implementations, a Euclidian distance between each pair of beats may be determined, and a median of these distances may be used in the present determination. In this example, current heartbeat interval 1210 is shown by the longer interval at the rightmost side of moving window 1220. Accordingly, an exemplary interval variability metric would be fairly large because current heartbeat interval 1210 is significantly different than the average heartbeat interval.

In another implementation, the interval variability metrics calculated above can be normalized by the number of heartbeat intervals (e.g., the size of the array). In yet other implementations, the interval variability metric can be normalized with the average interval. There can be any number of equivalent ways of calculating or normalizing the interval variability metric, such being explicitly contemplated by the present disclosure.

Figure 13:
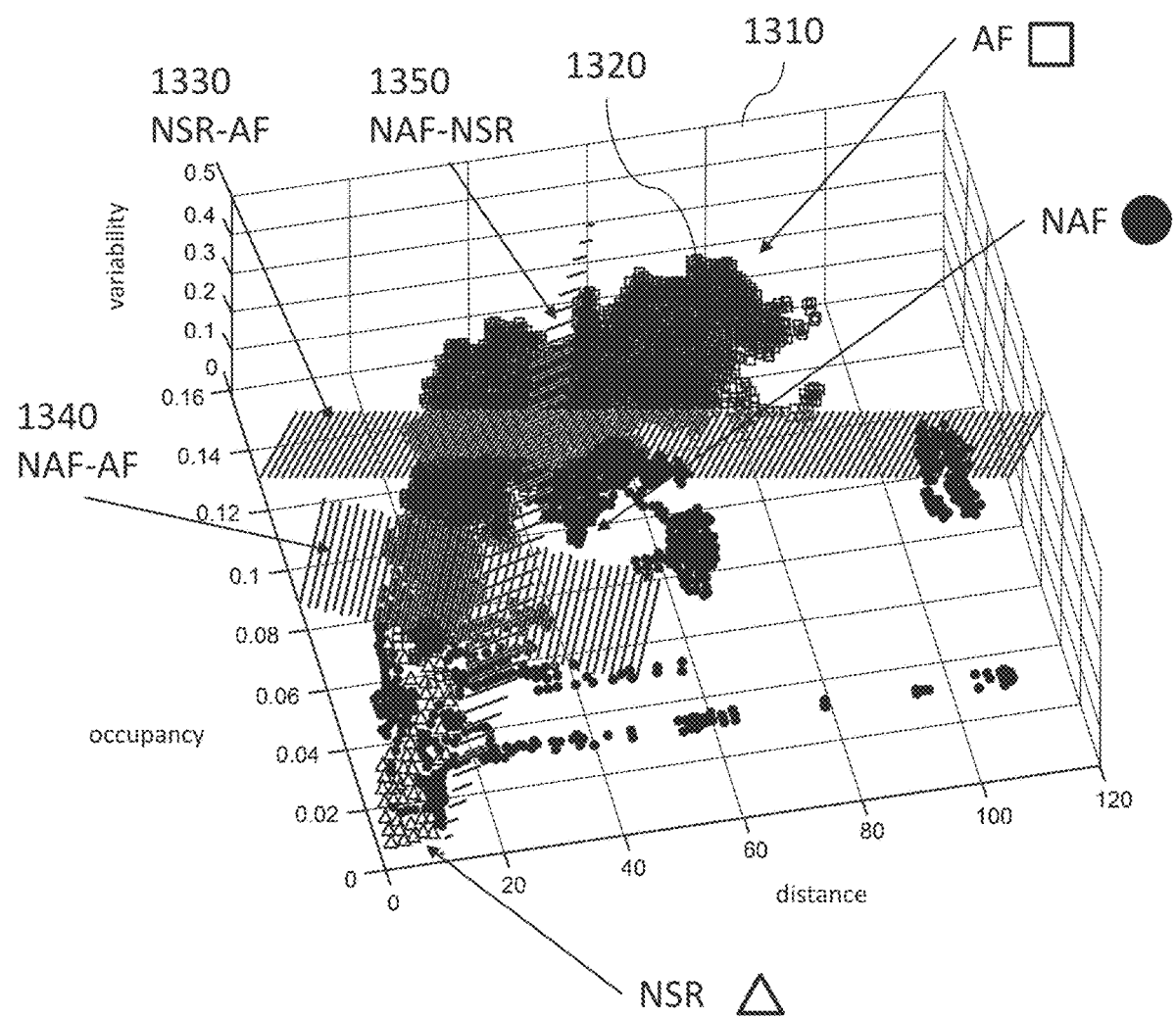
FIG. 13 is a diagram illustrating an exemplary method for determination of a three-dimensional space and discrimination planes for determining a heart rhythm type in accordance with certain aspects of the present disclosure.

FIG. 13 is a diagram illustrating A three-dimensional space 1310 and discrimination planes (1330, 1340, 1350) that may be used in an exemplary method for determining a heart rhythm type in accordance with certain aspects of the present disclosure. Determining the heart rhythm type can include utilization of the occupancy metric, the distance metric, and the interval variability metric, in relation to a three-dimensional space.

In certain implementations, the heart rhythm type can be determined based on any combination of the above metrics. For example, the heart rhythm type can be determined based solely on the occupancy metric, based solely on the distance metric, based solely on the interval variability metric, based on all three of the occupancy metric, the distance metric, and the interval variability metric, or any combination thereof.

FIG. 13 illustrates an exemplary implementation where the determination of a heart rhythm type is based at least on all three of an occupancy metric, a distance metric, and an interval variability metric. In the implementation illustrated, the points 1320 can be plotted in three-dimensional space 1310 defined at least by these three metrics.

In such a three-dimensional space, certain regions can be classified as corresponding to particular heart rhythm types delineated by one or more discrimination planes (1330, 1340, 1350). For example, referring to the NSR-AF plane 1330 depicted in FIG. 13, when a point is on one side of the NSR-AF plane 1330, such a point 1320 can be classified as referring to a heartbeat that is classified as NSR (normal sinus rhythm). Conversely, when a point is on the other side of the NSR-AF plane 1330, such a point can be classified as referring to heartbeat that is an AF rhythm type.

As illustrated in FIG. 13, in general, a regular heart rhythm would have points 1320 clustered toward the origin of the three-dimensional space (i.e., having low occupancy, distance, and variability). Locations further from the origin can indicate an irregular heart rhythm type of some type. The different exemplary symbols depicted in FIG. 13 indicate the heart rhythm types determined for a given point. For example, open triangles refer to heart rhythm types that are NSR, open squares refer to heart rhythm types that are AF, and solid circles refer to heart rhythm types that are NAF (i.e., not AF).

Discrimination planes (1330, 1340, 1350) can be computed automatically based on algorithms for how to define such planes. In other implementations, the discrimination planes (1330, 1340, 1350) can be determined from computational optimization of plane parameters (e.g., terms or coefficients in equations defining the discrimination planes (1330, 1340, 1350)) on annotated data. For example, it can be established that certain collections of points 1320 correspond to a particular heart rhythm type. The data can be annotated (e.g., by a physician adding tags, labels, or other metadata to the points in computer memory) to specify the heart rhythm type. Then, the discrimination planes (1330, 1340, 1350) can be computationally determined such that they best discriminate the classified points 1320. Similarly, such determinations can be made with machine learning.

Figure 14:
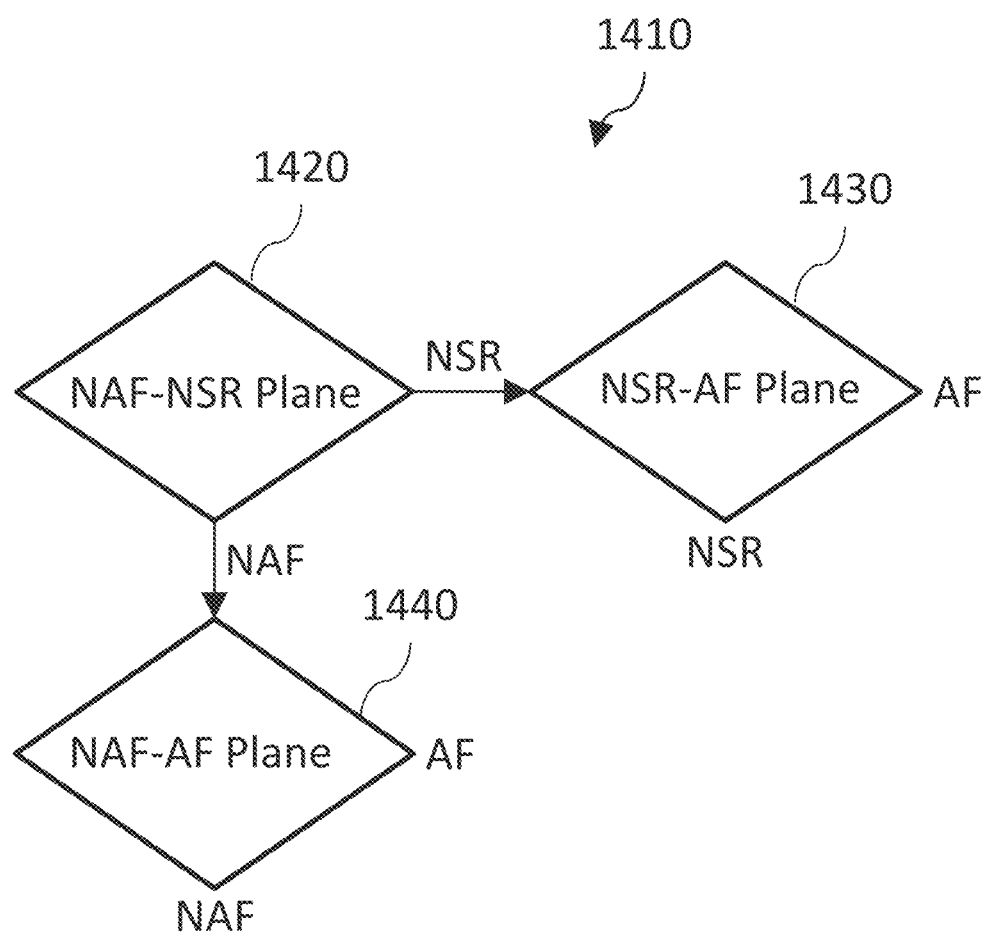
FIG. 14 is a diagram illustrating an exemplary decision tree for determining a heart rhythm type in accordance with certain aspects of the present disclosure.

FIG. 14 is a diagram illustrating a decision tree 1410 for an exemplary method for determining a heart rhythm type in accordance with certain aspects of the present disclosure. Because a given point 1320 can meet multiple criteria as defined by the discrimination planes, further rules can be implemented to determine the heart rhythm type. In general, implementations of rules for classifying a point as exhibiting a particular heart rhythm type can include first determining which side of a first discrimination plane the point is on, then determining which side of a second discrimination plane the point is on. For example, point 1320 can be on the NSR side of the NAF-NSR discrimination plane 1350 and also can be on the AF side of the NSR-AF discrimination plane 1330. The example decision tree 1440 shown in FIG. 14 illustrates one implementation for establishing a heart rhythm type based on the above considerations. Decision tree 1410 begins at NAF-NSR decision branch 1420 by first determining which side of the NAF-NSR plane 1350 the point is on. Then, if the point was on the NSR side, a second determination is made at NSR-AF decision branch 1430 as to which side of NSR-AF discrimination plane 1330 that point 1320 is on. When point 1320 is on the AF side, the heart rhythm type for that point 1320 is classified as AF. When point 1320 is on the NSR side, the heart rhythm type for that point 1320 is classified as NSR.

Returning to NAF-NSR decision branch 1420, when the point is on the NAF side of NAF-NSR discrimination plane 1350, a second determination can then be made at NF-AF decision branch 1440 whether the point is classified as NAF or AF based on which side of NAF-AF discrimination plane 1340 it is on.

The present disclosure explicitly contemplates other combinations of decision branches for classifying a point as AF, NSR, or NAF. Similarly, other rules can be added to further add conditions required for a particular classification, one example being that heartbeats (and points) which have been flagged as "noisy" are not used as a part of a dataset that serves as a basis for generating an AF alert.

In some implementations, the presence of a specific heart rhythm type can be established when a sufficient number of heart rhythm assessments are determined based on a local contiguous group of beats. In other words, the establishment of a particular heart rhythm type can be based on a) a sufficient number of classification determinations and b) requiring that the heartbeat intervals that establish a particular heart rhythm type are contiguous. The term "contiguous" means requiring that there are no invalid heartbeats in the heartbeat intervals. An invalid heartbeat can be, for example, determined based on the beat detection algorithm described herein or obtained during a period of noisy data (as detected by an accelerometer, other sensor, noise detection algorithm, etc.).

Certain implementations of the current subject can include different methods of classifying a particular point as having a specific heart rhythm type. For example, instead of utilizing discrimination planes, some implementations can include an algorithm implementing a series of conditional statements, thresholds, decision trees, or other such equivalent logical structures and flows to generate a classification of a point. For example, one implementation of such a conditional statement can be AF=(occupancy metric greater than 0.1, distance metric greater than 20, interval variability metric greater than 0.2). The previous example of a conditional statement implies three orthogonal discrimination planes (or thresholds). In other implementations, the discrimination planes need not be strictly planar but can instead be a surface which can contain any degree of local curvature or other shape. In general, the present disclosure contemplates a general partitioning of a space (of arbitrary dimension) into regions that can, at least in part, determine a particular heart rhythm type for a point in a particular region. Such regions can be one-dimensional (e.g. occupancy metric, distance metric, or interval variability metric greater than a predetermined value), two-dimensional (e.g. a specified area in a two dimensional space defined by the occupancy metric and the distance metric, three-dimensional (e.g., as illustrated by the example of FIG. 13), or higher dimension (e.g. where additional rules and metrics have been implemented to create an arbitrary number of factors that determine the heart rhythm type).

Some implementations of the current subject matter can include generating an output (e.g., a visualization) corresponding to the aforementioned points and plots and including, for example, any combination of the occupancy metric, the distance metric, the interval variability metric, an average heartbeat interval in a moving window, a first count of heartbeats for computing the occupancy metric in the moving window (optionally limited to qualified heartbeats), a second count of heartbeats for computing the distance metric in the moving window (optionally limited to qualified heartbeats), a third count of heartbeats for computing the interval variability metric in the moving window (optionally limited to qualified heartbeats), etc. Such output can be generated and provided, for example, to a user or healthcare provider, via an output device such as a smart phone, smartwatch, personal computer, or the like. The output can be provided in the form of an array or matrix (of arbitrary dimension), a data file, a graphical display such as a plot (such as illustrated by FIGS. 8-11) or chart, three-dimensional visualization (such as illustrated by FIG. 13), etc.

When an alert (e.g., indicating the presence of a particular heart rhythm type, such as AF) is needed, such alerts can be sent to and/or generated at any number or types of devices. Alerts can be sent to a wearable device, a computer or server, a smartphone (for example as used by a physician, a user, a caregiver, etc.), or the like. The alerts can be implemented as emails or text messages or may be audible, graphical, tactile (e.g., vibration), etc.

As described herein, certain implementations of the current subject matter can include providing an alert to a user based on the detection of a particular type of heart rhythm (e.g., AF). However, in some implementations, displaying of an AF detection alert may occur when AF has been determined based on a number of heartbeats greater than an AF detection alert threshold. For example, in theory, three heartbeats can be sufficient to determine AF based on some of the implementations described herein. However, it can be advantageous to rely on a larger set of data in order to obtain a more accurate determination of a particular heart rhythm type. For example, in some implementations, the minimum number of heartbeats (or points) required before generating an alert (e.g., an AF detection alert threshold) can be set to a predetermined number such as 50, 100, 200, etc. In some implementations, this alert detection threshold may be customizable (e.g., by a user, by a doctor or other caregivers, etc., via a user interface as described herein) such that a single AF beat may be cause for alarm for one user, but 50 AF beats, 100 AF beats, etc., may be required for other users. In some implementations, the AF detection threshold may be related to an amount of time a user experiences AF beats, and/or other AF related information.

In other implementations of the current subject matter, the system can require an (electronic) authorization before providing an AF detection alert to user. In some implementations, such an authorization can be electronically provided by an authorizing agent, such as a physician, a technician, a manufacturer, or other authorized person. The authorization can be stored, for example, as a part of a data file at any computing device in communication with the wearable device of a user. The authorization can further include an association between the authorization and a particular patient identification. For example, the authorization can indicate that the authorizing agent has authorized a particular user (having a patient identification such as a number, code, or the like) to receive alerts (e.g., an AF detection alert). Correspondingly, such an authorization can allow the wearable device to generate an alert only when such authorization exists (as verified at the wearable device, or any other computing system in communication with wearable device). Accordingly, such implementations can include receiving a patient identification communicated by the wearable device and generating the AF detection alert when an authorization is received that indicates a permission to display AF detection alerts to the user.

Implementations of the current subject matter can include, for example, performing calculations (e.g., determination of heartbeats, heartbeat intervals, processing of signal data, scaling of waveforms, etc.) as described herein, at any combination of computing systems and any combination of programmable processors distributed across the computing systems. Such computing systems can include smart phones, smartwatches, personal health monitoring devices, personal computers, laptop or tablet computers, cloud-based servers and networking environments, or the like, as further described herein. In this way, the present disclosure contemplates technical solutions that can be implemented at a single device, for example, by a smartwatch or personal health monitor. Other implementations of the technical solutions described herein can be distributed across multiple devices, for example, acquiring sensor data from a sensor in contact with a user, transmitting the sensor data from the sensing device to a remote computer such as a server, the server executing instructions to perform calculations on the data, and then transmission of data and/or commands to one or more recipient devices to cause the recipient devices to display a specific graphical output, generate an alert, etc.

Implementations of the current subject matter can include, but are not limited to, methods consistent with the descriptions provided herein as well as articles that comprise a tangibly embodied machine-readable medium operable to cause one or more machines (e.g., computers, etc.) to result in operations implementing one or more of the described features. Similarly, computer systems are also contemplated that may include one or more processors and one or more memories coupled to the one or more processors. A memory, which can include a computer-readable storage medium, may include, encode, store, or the like, one or more programs that cause one or more processors to perform one or more of the operations described herein. Computer implemented methods consistent with one or more implementations of the current subject matter can be implemented by one or more data processors residing in a single computing system or across multiple computing systems. Such multiple computing systems can be connected and can exchange data and/or commands or other instructions or the like via one or more connections, including but not limited to a connection over a network (e.g., the internet, a wireless wide area network, a local area network, a wide area network, a wired network, or the like), via a direct connection between one or more of the multiple computing systems, etc.

While certain features of the currently disclosed subject matter are described for illustrative purposes in relation to particular implementations, it should be readily understood that such features are not intended to be limiting. The claims that follow this disclosure are intended to define the scope of the protected subject matter.

Although a few embodiments have been described in detail above, other modifications are possible. For example, the method steps depicted in FIGS. 1 and 4 and described herein do not require the particular order shown, or sequential order, to achieve desirable results.

The present disclosure contemplates that the calculations disclosed in the embodiments herein may be performed in a number of ways, applying the same concepts taught herein, and that such calculations are equivalent to the embodiments disclosed.

One or more aspects or features of the subject matter described herein can be realized in digital electronic circuitry, integrated circuitry, specially designed application specific integrated circuits (ASICs), field programmable gate arrays (FPGAs) computer hardware, firmware, software, and/or combinations thereof. These various aspects or features can include implementation in one or more computer programs that are executable and/or interpretable on a programmable system including at least one programmable processor, which can be special or general purpose, coupled to receive data and instructions from, and to transmit data and instructions to, a storage system, at least one input device, and at least one output device. The programmable system or computing system may include clients and servers. A client and server are generally remote from each other and typically interact through a communication network. The relationship of client and server arises by virtue of computer programs running on the respective computers and having a client-server relationship to each other.

These computer programs, which can also be referred to programs, software, software applications, applications, components, or code, include machine instructions for a programmable processor, and can be implemented in a high-level procedural language, an object-oriented programming language, a functional programming language, a logical programming language, and/or in assembly/machine language. As used herein, the term "machine-readable medium" (or "computer readable medium") refers to any computer program product, apparatus and/or device, such as for example magnetic discs, optical disks, memory, and Programmable Logic Devices (PLDs), used to provide machine instructions and/or data to a programmable processor, including a machine-readable medium that receives machine instructions as a machine-readable signal. The term "machine-readable signal" (or "computer readable signal") refers to any signal used to provide machine instructions and/or data to a programmable processor. The machine-readable medium can store such machine instructions non-transitorily, such as for example as would a non-transient solid-state memory or a magnetic hard drive or any equivalent storage medium. The machine-readable medium can alternatively or additionally store such machine instructions in a transient manner, such as for example as would a processor cache or other random access memory associated with one or more physical processor cores.

To provide for interaction with a user, one or more aspects or features of the subject matter described herein can be implemented on a computer having a display device, such as for example a cathode ray tube (CRT) or a liquid crystal display (LCD) or a light emitting diode (LED) monitor for displaying information to the user and a keyboard and a pointing device, such as for example a mouse or a trackball, by which the user may provide input to the computer. Other kinds of devices can be used to provide for interaction with a user as well. For example, feedback provided to the user can be any form of sensory feedback, such as for example visual feedback, auditory feedback, or tactile feedback; and input from the user may be received in any form, including, but not limited to, acoustic, speech, or tactile input. Other possible input devices include, but are not limited to, touch screens or other touch-sensitive devices such as single or multi-point resistive or capacitive trackpads, voice recognition hardware and software, optical scanners, optical pointers, digital image capture devices and associated interpretation software, and the like.

In the descriptions above and in the claims, phrases such as "at least one of" or "one or more of" may occur followed by a conjunctive list of elements or features. The term "and/or" may also occur in a list of two or more elements or features. Unless otherwise implicitly or explicitly contradicted by the context in which it used, such a phrase is intended to mean any of the listed elements or features individually or any of the recited elements or features in combination with any of the other recited elements or features. For example, the phrases "at least one of A and B;" "one or more of A and B;" and "A and/or B" are each intended to mean "A alone, B alone, or A and B together." A similar interpretation is also intended for lists including three or more items. For example, the phrases "at least one of A, B, and C;" "one or more of A, B, and C;" and "A, B, and/or C" are each intended to mean "A alone, B alone, C alone, A and B together, A and C together, B and C together, or A and B and C together." Use of the term "based on," above and in the claims is intended to mean, "based at least in part on," such that an unrecited feature or element is also permissible.

The subject matter described herein can be embodied in systems, apparatus, methods, computer programs and/or articles depending on the desired configuration. Any methods or the logic flows depicted in the accompanying figures and/or described herein do not necessarily require the particular order shown, or sequential order, to achieve desirable results. The implementations set forth in the foregoing description do not represent all implementations consistent with the subject matter described herein. Instead, they are merely some examples consistent with aspects related to the described subject matter. Although a few variations have been described in detail above, other modifications or additions are possible. In particular, further features and/or variations can be provided in addition to those set forth herein. The implementations described above can be directed to various combinations and subcombinations of the disclosed features and/or combinations and subcombinations of further features noted above. Furthermore, above described advantages are not intended to limit the application of any issued claims to processes and structures accomplishing any or all of the advantages.

Additionally, section headings shall not limit or characterize the invention(s) set out in any claims that may issue from this disclosure. Specifically, and by way of example, although the headings refer to a "Technical Field," such claims should not be limited by the language chosen under this heading to describe the so-called technical field. Further, the description of a technology in the "Background" is not to be construed as an admission that technology is prior art to any invention(s) in this disclosure. Neither is the "Summary" to be considered as a characterization of the invention (s) set forth in issued claims. Furthermore, any reference to this disclosure in general or use of the word "invention" in the singular is not intended to imply any limitation on the scope of the claims set forth below. Multiple inventions may be set forth according to the limitations of the multiple claims issuing from this disclosure, and such claims accordingly define the invention(s), and their equivalents, that are protected thereby.

The invention claimed is:

1. A computer program product,
said computer program product being configured to be in communication with a PPG sensor,
said computer program product comprising a non-transitory, machine-readable medium storing instructions which, when executed by at least one programmable processor, caused at least one programmable processor to perform operations comprising:
receiving photoplethysmographic (PPG) signal data communicated by the PPG sensor of a wearable device worn by a user;
determining a plurality of heartbeats from at least a portion of the PPG signal data;
determining a heart rhythm type based on at least the plurality of heartbeats;
determining whether the heart rhythm type includes Atrial Fibrillation (AF) comprising utilization of an occupancy metric, a distance metric, and an interval variability metric, classifying regions corresponding to particular heart rhythm types as set apart by one or more discrimination planes in a three-dimensional space defined by the occupancy metric, the distance metric, and the interval variability metric, wherein AF is identified on an AF side of at least one of the one or more discrimination planes; and
displaying, when an AF is detected, a detection alert at the wearable device.

2. The computer program product of claim 1 wherein determination of whether the heart rhythm type is AF involves analyzing a point as being on either an AF side or a normal sinus rhythm (NSR) side of an NSR-AF plane.

3. The computer program product of claim 2 wherein the heart rhythm type is determined to be AF when the point is on the AF side of the NSR-AF plane.

4. The computer program product of claim 2 wherein the heart rhythm type is determined to be NSR when the point is on the NSR side of the NSR-AF plane.

5. The computer program product of claim 1 determination of whether the heart rhythm type is AF involves analyzing a point as being on either an AF side or a not AF (NAF) side of an NAF-AF plane.

6. The computer program product of claim 5 wherein the heart rhythm type is determined to be AF when the point is on the AF side of the NAF-AF plane.

7. The computer program product of claim 5 wherein the heart rhythm type is determined to be NAF when the point is on the NAF side of the NAF-AF plane.

8. A computer program product,
said computer program product being configured to be in communication with a PPG sensor,
said computer program product comprising a non-transitory, machine-readable medium storing instructions which, when executed by at least one programmable processor, caused at least one programmable processor to perform operations comprising:
receiving photoplethysmographic (PPG) signal data communicated by the PPG sensor of a wearable device worn by a user;
determining a plurality of heartbeats from at least a portion of the PPG signal data;
determining a heart rhythm type based on at least the plurality of heartbeats;
determining whether the heart rhythm type includes Atrial Fibrillation (AF) comprising utilization of an occupancy metric, a distance metric, and an interval variability metric, classifying regions corresponding to particular heart rhythm types as set apart by at least two discrimination planes in a three-dimensional space defined by the occupancy metric, the distance metric, and the interval variability metric, utilizing at least a two-step analysis via a decision tree; and
displaying, when an AF is detected, a detection alert at the wearable device.

9. The computer program product of claim 8 wherein the decision tree involves first analyzing a point as being on either a not AF (NAF) side or a normal sinus rhythm (NSR) side of an NAF-NSR plane.

10. The computer program product of claim 9 wherein when a point is identified on the NSR side of the NAF-NSR plane, then analyzing whether the point is on an AF side or a NSR side of an NSR-AF plane.

11. The computer program product of claim 10 wherein the heart rhythm type is determined to be AF when the point is on the AF side of the NSR-AF plane.

12. The computer program product of claim 10 wherein the heart rhythm type is determined to be NSR when the point is on the NSR side of the NSR-AF plane.

13. The computer program product of claim 9 wherein when a point is identified on an NAF side of the NAF-NSR plane, then analyzing whether the point is on an AF side or a NAF side of an NAF-AF plane.

14. The computer program product of claim 13 wherein the heart rhythm type is determined to be AF when the point is on the AF side of the NAF-AF plane.

15. The computer program product of claim 13 wherein the heart rhythm type is determined to be NAF when the point is on the NAF side of the NAF-AF plane.

* * * * *